(12) United States Patent
Zagury et al.

(10) Patent No.: US 9,301,997 B2
(45) Date of Patent: Apr. 5, 2016

(54) METHOD OF VACCINATION FOR LIMITING ARTICULAR INFLAMMATION IN RHEUMATOID ARTHRITIS AND MULTIPLE SCLEROSIS BY ADMINISTERING IL-23 PEPTIDES

(75) Inventors: Jean-François Zagury, Paris (FR); Rojo Ratsimandresy, Clichy (FR)

(73) Assignee: PEPTINOV SAS, Paris (FR)

( * ) Notice: Subject to any disclaimer, the term of this patent is extended or adjusted under 35 U.S.C. 154(b) by 0 days.

(21) Appl. No.: 13/497,372

(22) PCT Filed: Sep. 21, 2010

(86) PCT No.: PCT/IB2010/054264
§ 371 (c)(1),
(2), (4) Date: Jun. 29, 2012

(87) PCT Pub. No.: WO2011/033493
PCT Pub. Date: Mar. 24, 2011

(65) Prior Publication Data
US 2012/0269838 A1     Oct. 25, 2012

Related U.S. Application Data

(60) Provisional application No. 61/244,324, filed on Sep. 21, 2009.

(51) Int. Cl.
*A61K 38/10* (2006.01)
*A61K 39/00* (2006.01)
*C07K 16/24* (2006.01)

(52) U.S. Cl.
CPC ........... *A61K 39/0008* (2013.01); *C07K 16/244* (2013.01); *A61K 2039/55566* (2013.01); *A61K 2039/6081* (2013.01); *C07K 2317/34* (2013.01)

(58) Field of Classification Search
CPC ... A61K 38/2013; A61K 38/04; A61K 38/10; A61K 38/12
See application file for complete search history.

(56) References Cited

FOREIGN PATENT DOCUMENTS

| WO | 03/084979 A2 | 10/2003 |
|----|--------------|---------|
| WO | 2005/079837 A1 | 9/2005 |
| WO | 2005/108425 A1 | 11/2005 |
| WO | 2007/005647 A2 | 1/2007 |
| WO | 2008/103432 A1 | 8/2008 |

OTHER PUBLICATIONS

Vaknin-Dembinsky, Adi et al., "IL-23 Is Increased in Dendritic Cells in Multiple Sclerosis and Down-Regulation of IL-23 by Antisense Oligos Increases Dendritic Cell IL-10 Production," The Journal of Immunology, 2006, pp. 7768-7774, 2024-2025, The American Association of Immunologists, Inc., USA.

Langowski, John L. et al., "IL-23 Promotes Tumour Incidence and Growth," NATURE, Jul. 2006, vol. 442/27, pp. 461-465. Nature Publishing Group.

*Primary Examiner* — Prema Mertz
(74) *Attorney, Agent, or Firm* — Browdy and Neimark, PLLC

(57) ABSTRACT

The present invention relates to a pharmaceutical composition comprising as active substance, at least one compound comprising, or consisting of, a polypeptide which comprises, or consists of, at least 11 contiguous amino acids selected from $X_1$-S-D-I-F-$X_2$-G-E-P-$X_3$-L-$X_4$-P-$X_5$-$X_6$-$X_7$-$X_8$-$X_9$-Q-L (SEQ ID NO: 13).

14 Claims, 5 Drawing Sheets

SEQUENCE LISTING

<160> NUMBER OF SEQ ID NOS: 141

<210> SEQ ID NO 1
<211> LENGTH: 19
<212> TYPE: PRT
<213> ORGANISM: Homo Sapiens

<400> SEQUENCE: 1

Leu Leu Pro Asp Ser Pro Val Gly Gln Leu His Ala Ser Leu Leu Gly
1               5                   10                  15

Leu Ser Gln

<210> SEQ ID NO 2
<211> LENGTH: 20
<212> TYPE: PRT
<213> ORGANISM: Homo Sapiens

<400> SEQUENCE: 2

Gly Ser Asp Ile Phe Thr Gly Glu Pro Ser Leu Leu Pro Asp Ser Pro
1               5                   10                  15

Val Gly Gln Leu
            20

<210> SEQ ID NO 3
<211> LENGTH: 20
<212> TYPE: PRT
<213> ORGANISM: Mus Musculus

<400> SEQUENCE: 3

Asp Ser Asp Ile Phe Lys Gly Glu Pro Ala Leu Leu Pro Asp Ser Pro
1               5                   10                  15

Met Glu Gln Leu
            20

<210> SEQ ID NO 4
<211> LENGTH: 11
<212> TYPE: PRT
<213> ORGANISM: Mus Musculus

<400> SEQUENCE: 4

Lys Gly Glu Pro Ala Leu Leu Pro Asp Ser Pro
1               5                   10

<210> SEQ ID NO 5
<211> LENGTH: 11
<212> TYPE: PRT
<213> ORGANISM: Homo Sapiens

<400> SEQUENCE: 5

Thr Gly Glu Pro Ser Leu Leu Pro Asp Ser Pro
1               5                   10

<210> SEQ ID NO 6
<211> LENGTH: 7
<212> TYPE: PRT
<213> ORGANISM: Artificial
<220> FEATURE:
<223> OTHER INFORMATION: sub-sequence of seq ID NO2 with C-terminal and
      N-terminal cystein

<400> SEQUENCE: 6

Cys Thr Gly Glu Pro Ser Cys
1               5

<210> SEQ ID NO 7
<211> LENGTH: 8
<212> TYPE: PRT
<213> ORGANISM: Artificial
<220> FEATURE:
<223> OTHER INFORMATION: sub-sequence of seq ID NO2 with  N-terminal
      cystein and C-terminal cystein and tyrosin

<400> SEQUENCE: 7

Cys Leu Pro Asp Ser Pro Cys Tyr

<210> SEQ ID NO 8
<211> LENGTH: 15
<212> TYPE: PRT
<213> ORGANISM: Artificial
<220> FEATURE:
<223> OTHER INFORMATION: reverse sequence derived from SEQ ID NO2

<400> SEQUENCE: 8

Val Pro Ser Asp Pro Leu Leu Ser Pro Glu Gly Thr Phe Ile Asp
1               5                   10                  15

<210> SEQ ID NO 9
<211> LENGTH: 11
<212> TYPE: PRT
<213> ORGANISM: Artificial
<220> FEATURE:
<223> OTHER INFORMATION: polypeptide
<220> FEATURE:
<221> NAME/KEY: MISC_FEATURE
<222> LOCATION: (1)..(1)
<223> OTHER INFORMATION: T or K
<220> FEATURE:
<221> NAME/KEY: MISC_FEATURE
<222> LOCATION: (5)..(5)
<223> OTHER INFORMATION: S or P or A
<220> FEATURE:
<221> NAME/KEY: MISC_FEATURE
<222> LOCATION: (7)..(7)
<223> OTHER INFORMATION: L or F or H
<220> FEATURE:
<221> NAME/KEY: MISC_FEATURE
<222> LOCATION: (9)..(9)
<223> OTHER INFORMATION: D or N
<220> FEATURE:
<221> NAME/KEY: MISC_FEATURE
<222> LOCATION: (10)..(10)
<223> OTHER INFORMATION: S or G or D
<220> FEATURE:
<221> NAME/KEY: MISC_FEATURE
<222> LOCATION: (11)..(11)
<223> OTHER INFORMATION: P or S

<400> SEQUENCE: 9

Xaa Gly Glu Pro Xaa Leu Xaa Pro Xaa Xaa Xaa
1               5                   10

<210> SEQ ID NO 10
<211> LENGTH: 11
<212> TYPE: PRT
<213> ORGANISM: Canis lupus familiaris

<400> SEQUENCE: 10

Thr Gly Glu Pro Ser Leu Leu Pro Asp Gly Pro
1               5                   10

<210> SEQ ID NO 11
<211> LENGTH: 11
<212> TYPE: PRT
<213> ORGANISM: Peromyscus maniculatus

<400> SEQUENCE: 11

Thr Gly Glu Pro Ser Leu Leu Pro Asp Asp Pro
1               5                   10

<210> SEQ ID NO 12
<211> LENGTH: 11
<212> TYPE: PRT
<213> ORGANISM: Equus caballus

```
<400> SEQUENCE: 12

Thr Gly Glu Pro Ser Leu Leu Pro Asn Gly Pro
1               5                   10

<210> SEQ ID NO 13
<211> LENGTH: 20
<212> TYPE: PRT
<213> ORGANISM: Artificial
<220> FEATURE:
<223> OTHER INFORMATION: polypeptide
<220> FEATURE:
<221> NAME/KEY: MISC_FEATURE
<222> LOCATION: (1)..(1)
<223> OTHER INFORMATION: G or D or A
<220> FEATURE:
<221> NAME/KEY: MISC_FEATURE
<222> LOCATION: (6)..(6)
<223> OTHER INFORMATION: T or K
<220> FEATURE:
<221> NAME/KEY: MISC_FEATURE
<222> LOCATION: (10)..(10)
<223> OTHER INFORMATION: S or P or A
<220> FEATURE:
<221> NAME/KEY: MISC_FEATURE
<222> LOCATION: (12)..(12)
<223> OTHER INFORMATION: L or F or H
<220> FEATURE:
<221> NAME/KEY: MISC_FEATURE
<222> LOCATION: (14)..(14)
<223> OTHER INFORMATION: D or N
<220> FEATURE:
<221> NAME/KEY: MISC_FEATURE
<222> LOCATION: (15)..(15)
<223> OTHER INFORMATION: S or G or D
<220> FEATURE:
<221> NAME/KEY: MISC_FEATURE
<222> LOCATION: (16)..(16)
<223> OTHER INFORMATION: P or S
<220> FEATURE:
<221> NAME/KEY: MISC_FEATURE
<222> LOCATION: (17)..(17)
<223> OTHER INFORMATION: V or M
<220> FEATURE:
<221> NAME/KEY: MISC_FEATURE
<222> LOCATION: (18)..(18)
<223> OTHER INFORMATION: G or S or E or D or A

<400> SEQUENCE: 13

Xaa Ser Asp Ile Phe Xaa Gly Glu Pro Xaa Leu Xaa Pro Xaa Xaa Xaa
1               5                   10                  15

Xaa Xaa Gln Leu
        20

<210> SEQ ID NO 14
<211> LENGTH: 20
<212> TYPE: PRT
<213> ORGANISM: Canis lupus familiaris

<400> SEQUENCE: 14

Gly Ser Asp Ile Phe Thr Gly Glu Pro Ser Leu Leu Pro Asp Gly Pro
1               5                   10                  15

Val Gly Gln Leu
        20

<210> SEQ ID NO 15
<211> LENGTH: 20
<212> TYPE: PRT
<213> ORGANISM: Rattus norvegicus

<400> SEQUENCE: 15
```

```
<210> SEQ ID NO 16
<211> LENGTH: 20
<212> TYPE: PRT
<213> ORGANISM: Peromyscus maniculatus

<400> SEQUENCE: 16

Asp Ser Asp Ile Phe Thr Gly Glu Pro Ser Leu Leu Pro Asp Asp Pro
1               5                   10                  15

Val Gly Gln Leu
            20

<210> SEQ ID NO 17
<211> LENGTH: 20
<212> TYPE: PRT
<213> ORGANISM: Onychomys leucogaster

<400> SEQUENCE: 17

Asp Ser Asp Ile Phe Thr Gly Glu Pro Ser Leu Leu Pro Asp Gly Pro
1               5                   10                  15

Val Gly Gln Leu
            20

<210> SEQ ID NO 18
<211> LENGTH: 20
<212> TYPE: PRT
<213> ORGANISM: Cervus elaphus

<400> SEQUENCE: 18

Gly Ser Asp Ile Phe Thr Gly Glu Pro Ser Leu Leu Pro Asp Gly Pro
1               5                   10                  15

Val Asp Gln Leu
            20

<210> SEQ ID NO 19
<211> LENGTH: 20
<212> TYPE: PRT
<213> ORGANISM: Equus caballus

<400> SEQUENCE: 19

Gly Ser Asp Ile Phe Thr Gly Glu Pro Ser Leu Leu Pro Asn Gly Pro
1               5                   10                  15

Val Asp Gln Leu
            20

<210> SEQ ID NO 20
<211> LENGTH: 20
<212> TYPE: PRT
<213> ORGANISM: Bos taurus

<400> SEQUENCE: 20

Gly Ser Asp Ile Phe Thr Gly Glu Pro Ser Leu Leu Pro Asn Gly Pro
1               5                   10                  15

Val Asp Gln Leu
            20

<210> SEQ ID NO 21
```

(Continuation of prior SEQ ID NO 15:)

Asp Ser Asp Ile Phe Thr Gly Glu Pro Ser Leu Leu Pro Asp Ser Pro
1               5                   10                  15

Val Asp Gln Leu
            20

```
<211> LENGTH: 20
<212> TYPE: PRT
<213> ORGANISM: Sus scrofa

<400> SEQUENCE: 21

Gly Ser Asp Ile Phe Thr Gly Glu Pro Ser Leu His Pro Asp Gly Ser
1               5                   10                  15

Val Gly Gln Leu
            20

<210> SEQ ID NO 22
<211> LENGTH: 20
<212> TYPE: PRT
<213> ORGANISM: Cavia porcellus

<400> SEQUENCE: 22

Gly Ser Asp Ile Phe Thr Gly Glu Pro Pro Leu Phe Pro Asp Gly Pro
1               5                   10                  15

Val Ser Gln Leu
            20

<210> SEQ ID NO 23
<211> LENGTH: 20
<212> TYPE: PRT
<213> ORGANISM: Mus musculus

<400> SEQUENCE: 23

Asp Ser Asp Ile Phe Lys Gly Glu Pro Ala Leu Leu Pro Asp Ser Pro
1               5                   10                  15

Met Glu Gln Leu
            20

<210> SEQ ID NO 24
<211> LENGTH: 20
<212> TYPE: PRT
<213> ORGANISM: Homo Sapiens

<400> SEQUENCE: 24

Gly Ser Asp Ile Phe Thr Gly Glu Pro Ser Leu Leu Pro Asp Ser Pro
1               5                   10                  15

Val Gly Gln Leu
            20

<210> SEQ ID NO 25
<211> LENGTH: 11
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (1)..(1)
<223> OTHER INFORMATION: Xaa can be G, D, or A
<220> FEATURE:
<221> NAME/KEY: misc_feature
<222> LOCATION: (6)..(6)
<223> OTHER INFORMATION: Xaa can be T or K
<220> FEATURE:
<221> NAME/KEY: misc_feature
<222> LOCATION: (10)..(10)
<223> OTHER INFORMATION: Xaa can be S, P, or A

<400> SEQUENCE: 25

Xaa Ser Asp Ile Phe Xaa Gly Glu Pro Xaa Leu
1               5                   10
```

```
<210> SEQ ID NO 26
<211> LENGTH: 11
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (5)..(5)
<223> OTHER INFORMATION: Xaa can be T or K
<220> FEATURE:
<221> NAME/KEY: misc_feature
<222> LOCATION: (9)..(9)
<223> OTHER INFORMATION: Xaa can be S, P, or A
<220> FEATURE:
<221> NAME/KEY: misc_feature
<222> LOCATION: (11)..(11)
<223> OTHER INFORMATION: Xaa can be L, H, or F

<400> SEQUENCE: 26

Ser Asp Ile Phe Xaa Gly Glu Pro Xaa Leu Xaa
1               5                   10

<210> SEQ ID NO 27
<211> LENGTH: 11
<212> TYPE: PRT
<213> ORGANISM: Artificial sequence
<220> FEATURE:
<223> OTHER INFORMATION: IL23p19 fragment
<220> FEATURE:
<221> NAME/KEY: misc_feature
<222> LOCATION: (4)..(4)
<223> OTHER INFORMATION: Xaa can be T or K
<220> FEATURE:
<221> NAME/KEY: misc_feature
<222> LOCATION: (8)..(8)
<223> OTHER INFORMATION: Xaa can be S, P, or A
<220> FEATURE:
<221> NAME/KEY: misc_feature
<222> LOCATION: (10)..(10)
<223> OTHER INFORMATION: Xaa can be L, H, or F

<400> SEQUENCE: 27

Asp Ile Phe Xaa Gly Glu Pro Xaa Leu Xaa Pro
1               5                   10

<210> SEQ ID NO 28
<211> LENGTH: 11
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (3)..(3)
<223> OTHER INFORMATION: Xaa can be T or K
<220> FEATURE:
<221> NAME/KEY: misc_feature
<222> LOCATION: (7)..(7)
<223> OTHER INFORMATION: Xaa can be S, P, or A
<220> FEATURE:
<221> NAME/KEY: misc_feature
<222> LOCATION: (9)..(9)
<223> OTHER INFORMATION: Xaa can be L, H, or F
<220> FEATURE:
<221> NAME/KEY: misc_feature
<222> LOCATION: (11)..(11)
<223> OTHER INFORMATION: Xaa can be D or N

<400> SEQUENCE: 28

Ile Phe Xaa Gly Glu Pro Xaa Leu Xaa Pro Xaa
1               5                   10
```

```
<210> SEQ ID NO 29
<211> LENGTH: 11
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (2)..(2)
<223> OTHER INFORMATION: Xaa can be T or K
<220> FEATURE:
<221> NAME/KEY: misc_feature
<222> LOCATION: (6)..(6)
<223> OTHER INFORMATION: Xaa can be S, P, or A
<220> FEATURE:
<221> NAME/KEY: misc_feature
<222> LOCATION: (8)..(8)
<223> OTHER INFORMATION: Xaa can be L, H, or F
<220> FEATURE:
<221> NAME/KEY: misc_feature
<222> LOCATION: (10)..(10)
<223> OTHER INFORMATION: Xaa can be D or N
<220> FEATURE:
<221> NAME/KEY: misc_feature
<222> LOCATION: (11)..(11)
<223> OTHER INFORMATION: Xaa can be G, S, or D

<400> SEQUENCE: 29

Phe Xaa Gly Glu Pro Xaa Leu Xaa Pro Xaa Xaa
1               5                   10

<210> SEQ ID NO 30
<211> LENGTH: 11
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (1)..(1)
<223> OTHER INFORMATION: Xaa can be T or K
<220> FEATURE:
<221> NAME/KEY: misc_feature
<222> LOCATION: (5)..(5)
<223> OTHER INFORMATION: Xaa can be S, P, or A
<220> FEATURE:
<221> NAME/KEY: misc_feature
<222> LOCATION: (7)..(7)
<223> OTHER INFORMATION: Xaa can be L, H, or F
<220> FEATURE:
<221> NAME/KEY: misc_feature
<222> LOCATION: (9)..(9)
<223> OTHER INFORMATION: Xaa can be D or N
<220> FEATURE:
<221> NAME/KEY: misc_feature
<222> LOCATION: (10)..(10)
<223> OTHER INFORMATION: Xaa can be G, S, or D
<220> FEATURE:
<221> NAME/KEY: misc_feature
<222> LOCATION: (11)..(11)
<223> OTHER INFORMATION: Xaa can be P or S

<400> SEQUENCE: 30

Xaa Gly Glu Pro Xaa Leu Xaa Pro Xaa Xaa Xaa
1               5                   10

<210> SEQ ID NO 31
<211> LENGTH: 11
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
```

```
<222> LOCATION: (4)..(4)
<223> OTHER INFORMATION: Xaa can be S, P, or A
<220> FEATURE:
<221> NAME/KEY: misc_feature
<222> LOCATION: (6)..(6)
<223> OTHER INFORMATION: Xaa can be L, H, or F
<220> FEATURE:
<221> NAME/KEY: misc_feature
<222> LOCATION: (8)..(8)
<223> OTHER INFORMATION: Xaa can be D or N
<220> FEATURE:
<221> NAME/KEY: misc_feature
<222> LOCATION: (9)..(9)
<223> OTHER INFORMATION: Xaa can be G, S, or D
<220> FEATURE:
<221> NAME/KEY: misc_feature
<222> LOCATION: (10)..(10)
<223> OTHER INFORMATION: Xaa can be P or S
<220> FEATURE:
<221> NAME/KEY: misc_feature
<222> LOCATION: (11)..(11)
<223> OTHER INFORMATION: Xaa can be V or M

<400> SEQUENCE: 31

Gly Glu Pro Xaa Leu Xaa Pro Xaa Xaa Xaa Xaa
1               5                   10

<210> SEQ ID NO 32
<211> LENGTH: 11
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (3)..(3)
<223> OTHER INFORMATION: Xaa can be S, P, or A
<220> FEATURE:
<221> NAME/KEY: misc_feature
<222> LOCATION: (5)..(5)
<223> OTHER INFORMATION: Xaa can be L, H, or F
<220> FEATURE:
<221> NAME/KEY: misc_feature
<222> LOCATION: (7)..(7)
<223> OTHER INFORMATION: Xaa can be D or N
<220> FEATURE:
<221> NAME/KEY: misc_feature
<222> LOCATION: (8)..(8)
<223> OTHER INFORMATION: Xaa can be G, S, or D
<220> FEATURE:
<221> NAME/KEY: misc_feature
<222> LOCATION: (9)..(9)
<223> OTHER INFORMATION: Xaa can be P or S
<220> FEATURE:
<221> NAME/KEY: misc_feature
<222> LOCATION: (10)..(10)
<223> OTHER INFORMATION: Xaa can be V or M
<220> FEATURE:
<221> NAME/KEY: misc_feature
<222> LOCATION: (11)..(11)
<223> OTHER INFORMATION: Xaa can be G, D, S, E, or A

<400> SEQUENCE: 32

Glu Pro Xaa Leu Xaa Pro Xaa Xaa Xaa Xaa Xaa
1               5                   10

<210> SEQ ID NO 33
<211> LENGTH: 11
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (2)..(2)
```

```
<223> OTHER INFORMATION: Xaa can be S, P, or A
<220> FEATURE:
<221> NAME/KEY: misc_feature
<222> LOCATION: (4)..(4)
<223> OTHER INFORMATION: Xaa can be L, H, or F
<220> FEATURE:
<221> NAME/KEY: misc_feature
<222> LOCATION: (6)..(6)
<223> OTHER INFORMATION: Xaa can be D or N
<220> FEATURE:
<221> NAME/KEY: misc_feature
<222> LOCATION: (7)..(7)
<223> OTHER INFORMATION: Xaa can be G, S, or D
<220> FEATURE:
<221> NAME/KEY: misc_feature
<222> LOCATION: (8)..(8)
<223> OTHER INFORMATION: Xaa can be P or S
<220> FEATURE:
<221> NAME/KEY: misc_feature
<222> LOCATION: (9)..(9)
<223> OTHER INFORMATION: Xaa can be V or M
<220> FEATURE:
<221> NAME/KEY: misc_feature
<222> LOCATION: (10)..(10)
<223> OTHER INFORMATION: Xaa can be G, D, S, E, or A

<400> SEQUENCE: 33

Pro Xaa Leu Xaa Pro Xaa Xaa Xaa Xaa Xaa Gln
1               5                   10

<210> SEQ ID NO 34
<211> LENGTH: 11
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (1)..(1)
<223> OTHER INFORMATION: Xaa can be S, P, or A
<220> FEATURE:
<221> NAME/KEY: misc_feature
<222> LOCATION: (3)..(3)
<223> OTHER INFORMATION: Xaa can be L, H, or F
<220> FEATURE:
<221> NAME/KEY: misc_feature
<222> LOCATION: (5)..(5)
<223> OTHER INFORMATION: Xaa can be D or N
<220> FEATURE:
<221> NAME/KEY: misc_feature
<222> LOCATION: (6)..(6)
<223> OTHER INFORMATION: Xaa can be G, S, or D
<220> FEATURE:
<221> NAME/KEY: misc_feature
<222> LOCATION: (7)..(7)
<223> OTHER INFORMATION: Xaa can be P or S
<220> FEATURE:
<221> NAME/KEY: misc_feature
<222> LOCATION: (8)..(8)
<223> OTHER INFORMATION: Xaa can be V or M
<220> FEATURE:
<221> NAME/KEY: misc_feature
<222> LOCATION: (9)..(9)
<223> OTHER INFORMATION: Xaa can be G, D, S, E, or A

<400> SEQUENCE: 34

Xaa Leu Xaa Pro Xaa Xaa Xaa Xaa Xaa Gln Leu
1               5                   10

<210> SEQ ID NO 35
<211> LENGTH: 12
<212> TYPE: PRT
<213> ORGANISM: Artificial sequence
<220> FEATURE:
<223> OTHER INFORMATION: IL-23p19 fragment
```

```
<220> FEATURE:
<221> NAME/KEY: misc_feature
<222> LOCATION: (1)..(1)
<223> OTHER INFORMATION: Xaa can be G, D, or A
<220> FEATURE:
<221> NAME/KEY: misc_feature
<222> LOCATION: (6)..(6)
<223> OTHER INFORMATION: Xaa can be T or K
<220> FEATURE:
<221> NAME/KEY: misc_feature
<222> LOCATION: (10)..(10)
<223> OTHER INFORMATION: Xaa can be S, P, or A
<220> FEATURE:
<221> NAME/KEY: misc_feature
<222> LOCATION: (12)..(12)
<223> OTHER INFORMATION: Xaa can be L, H, or F

<400> SEQUENCE: 35

Xaa Ser Asp Ile Phe Xaa Gly Glu Pro Xaa Leu Xaa
1               5                   10

<210> SEQ ID NO 36
<211> LENGTH: 12
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (5)..(5)
<223> OTHER INFORMATION: Xaa can be T or K
<220> FEATURE:
<221> NAME/KEY: misc_feature
<222> LOCATION: (9)..(9)
<223> OTHER INFORMATION: Xaa can be S, P, or A
<220> FEATURE:
<221> NAME/KEY: misc_feature
<222> LOCATION: (11)..(11)
<223> OTHER INFORMATION: Xaa can be L, H, or F

<400> SEQUENCE: 36

Ser Asp Ile Phe Xaa Gly Glu Pro Xaa Leu Xaa Pro
1               5                   10

<210> SEQ ID NO 37
<211> LENGTH: 12
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (4)..(4)
<223> OTHER INFORMATION: Xaa can be T or K
<220> FEATURE:
<221> NAME/KEY: misc_feature
<222> LOCATION: (8)..(8)
<223> OTHER INFORMATION: Xaa can be S, P, or A
<220> FEATURE:
<221> NAME/KEY: misc_feature
<222> LOCATION: (10)..(10)
<223> OTHER INFORMATION: Xaa can be L, H, or F
<220> FEATURE:
<221> NAME/KEY: misc_feature
<222> LOCATION: (12)..(12)
<223> OTHER INFORMATION: Xaa can be D or N

<400> SEQUENCE: 37

Asp Ile Phe Xaa Gly Glu Pro Xaa Leu Xaa Pro Xaa
1               5                   10

<210> SEQ ID NO 38
<211> LENGTH: 12
```

```
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (3)..(3)
<223> OTHER INFORMATION: Xaa can be T or K
<220> FEATURE:
<221> NAME/KEY: misc_feature
<222> LOCATION: (7)..(7)
<223> OTHER INFORMATION: Xaa can be S, P, or A
<220> FEATURE:
<221> NAME/KEY: misc_feature
<222> LOCATION: (9)..(9)
<223> OTHER INFORMATION: Xaa can be L, H, or F
<220> FEATURE:
<221> NAME/KEY: misc_feature
<222> LOCATION: (11)..(11)
<223> OTHER INFORMATION: Xaa can be D or N
<220> FEATURE:
<221> NAME/KEY: misc_feature
<222> LOCATION: (12)..(12)
<223> OTHER INFORMATION: Xaa can be G, S, or D

<400> SEQUENCE: 38

Ile Phe Xaa Gly Glu Pro Xaa Leu Xaa Pro Xaa Xaa
1               5                   10

<210> SEQ ID NO 39
<211> LENGTH: 12
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (2)..(2)
<223> OTHER INFORMATION: Xaa can be T or K
<220> FEATURE:
<221> NAME/KEY: misc_feature
<222> LOCATION: (6)..(6)
<223> OTHER INFORMATION: Xaa can be S, P, or A
<220> FEATURE:
<221> NAME/KEY: misc_feature
<222> LOCATION: (8)..(8)
<223> OTHER INFORMATION: Xaa can be L, H, or F
<220> FEATURE:
<221> NAME/KEY: misc_feature
<222> LOCATION: (10)..(10)
<223> OTHER INFORMATION: Xaa can be D or N
<220> FEATURE:
<221> NAME/KEY: misc_feature
<222> LOCATION: (11)..(11)
<223> OTHER INFORMATION: Xaa can be G, S, or D
<220> FEATURE:
<221> NAME/KEY: misc_feature
<222> LOCATION: (12)..(12)
<223> OTHER INFORMATION: Xaa can be P or S

<400> SEQUENCE: 39

Phe Xaa Gly Glu Pro Xaa Leu Xaa Pro Xaa Xaa Xaa
1               5                   10

<210> SEQ ID NO 40
<211> LENGTH: 12
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (1)..(1)
<223> OTHER INFORMATION: Xaa can be T or K
<220> FEATURE:
```

<221> NAME/KEY: misc_feature
<222> LOCATION: (5)..(5)
<223> OTHER INFORMATION: Xaa can be S, P, or A
<220> FEATURE:
<221> NAME/KEY: misc_feature
<222> LOCATION: (7)..(7)
<223> OTHER INFORMATION: Xaa can be L, H, or F
<220> FEATURE:
<221> NAME/KEY: misc_feature
<222> LOCATION: (9)..(9)
<223> OTHER INFORMATION: Xaa can be D or N
<220> FEATURE:
<221> NAME/KEY: misc_feature
<222> LOCATION: (10)..(10)
<223> OTHER INFORMATION: Xaa can be G, S, or D
<220> FEATURE:
<221> NAME/KEY: misc_feature
<222> LOCATION: (11)..(11)
<223> OTHER INFORMATION: Xaa can be P or S
<220> FEATURE:
<221> NAME/KEY: misc_feature
<222> LOCATION: (12)..(12)
<223> OTHER INFORMATION: Xaa can be V or M

<400> SEQUENCE: 40

Xaa Gly Glu Pro Xaa Leu Xaa Pro Xaa Xaa Xaa Xaa
1               5                   10

<210> SEQ ID NO 41
<211> LENGTH: 12
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (4)..(4)
<223> OTHER INFORMATION: Xaa can be S, P, or A
<220> FEATURE:
<221> NAME/KEY: misc_feature
<222> LOCATION: (6)..(6)
<223> OTHER INFORMATION: Xaa can be L, H, or F
<220> FEATURE:
<221> NAME/KEY: misc_feature
<222> LOCATION: (8)..(8)
<223> OTHER INFORMATION: Xaa can be D or N
<220> FEATURE:
<221> NAME/KEY: misc_feature
<222> LOCATION: (9)..(9)
<223> OTHER INFORMATION: Xaa can be G, S, or D
<220> FEATURE:
<221> NAME/KEY: misc_feature
<222> LOCATION: (10)..(10)
<223> OTHER INFORMATION: Xaa can be P or S
<220> FEATURE:
<221> NAME/KEY: misc_feature
<222> LOCATION: (11)..(11)
<223> OTHER INFORMATION: Xaa can be V or M
<220> FEATURE:
<221> NAME/KEY: misc_feature
<222> LOCATION: (12)..(12)
<223> OTHER INFORMATION: Xaa can be G, D, S, E, or A

<400> SEQUENCE: 41

Gly Glu Pro Xaa Leu Xaa Pro Xaa Xaa Xaa Xaa Xaa
1               5                   10

<210> SEQ ID NO 42
<211> LENGTH: 12
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature

```
<222> LOCATION: (3)..(3)
<223> OTHER INFORMATION: Xaa can be S, P, or A
<220> FEATURE:
<221> NAME/KEY: misc_feature
<222> LOCATION: (5)..(5)
<223> OTHER INFORMATION: Xaa can be L, H, or F
<220> FEATURE:
<221> NAME/KEY: misc_feature
<222> LOCATION: (7)..(7)
<223> OTHER INFORMATION: Xaa can be D or N
<220> FEATURE:
<221> NAME/KEY: misc_feature
<222> LOCATION: (8)..(8)
<223> OTHER INFORMATION: Xaa can be G, S, or D
<220> FEATURE:
<221> NAME/KEY: misc_feature
<222> LOCATION: (9)..(9)
<223> OTHER INFORMATION: Xaa can be P or S
<220> FEATURE:
<221> NAME/KEY: misc_feature
<222> LOCATION: (10)..(10)
<223> OTHER INFORMATION: Xaa can be V or M
<220> FEATURE:
<221> NAME/KEY: misc_feature
<222> LOCATION: (11)..(11)
<223> OTHER INFORMATION: Xaa can be G, D, S, E, or A

<400> SEQUENCE: 42

Glu Pro Xaa Leu Xaa Pro Xaa Xaa Xaa Xaa Xaa Gln
1               5                   10

<210> SEQ ID NO 43
<211> LENGTH: 12
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (2)..(2)
<223> OTHER INFORMATION: Xaa can be S, P, or A
<220> FEATURE:
<221> NAME/KEY: misc_feature
<222> LOCATION: (4)..(4)
<223> OTHER INFORMATION: Xaa can be L, H, or F
<220> FEATURE:
<221> NAME/KEY: misc_feature
<222> LOCATION: (6)..(6)
<223> OTHER INFORMATION: Xaa can be D or N
<220> FEATURE:
<221> NAME/KEY: misc_feature
<222> LOCATION: (7)..(7)
<223> OTHER INFORMATION: Xaa can be G, S, or D
<220> FEATURE:
<221> NAME/KEY: misc_feature
<222> LOCATION: (8)..(8)
<223> OTHER INFORMATION: Xaa can be P or S
<220> FEATURE:
<221> NAME/KEY: misc_feature
<222> LOCATION: (9)..(9)
<223> OTHER INFORMATION: Xaa can be V or M
<220> FEATURE:
<221> NAME/KEY: misc_feature
<222> LOCATION: (10)..(10)
<223> OTHER INFORMATION: Xaa can be G, D, S, E, or A

<400> SEQUENCE: 43

Pro Xaa Leu Xaa Pro Xaa Xaa Xaa Xaa Xaa Gln Leu
1               5                   10

<210> SEQ ID NO 44
<211> LENGTH: 13
<212> TYPE: PRT
<213> ORGANISM: Artificial sequence
<220> FEATURE:
```

```
<223> OTHER INFORMATION: IL-23p19 fragment
<220> FEATURE:
<221> NAME/KEY: misc_feature
<222> LOCATION: (1)..(1)
<223> OTHER INFORMATION: Xaa can be G, D, or A
<220> FEATURE:
<221> NAME/KEY: misc_feature
<222> LOCATION: (6)..(6)
<223> OTHER INFORMATION: Xaa can be T or K
<220> FEATURE:
<221> NAME/KEY: misc_feature
<222> LOCATION: (10)..(10)
<223> OTHER INFORMATION: Xaa can be S, P, or A
<220> FEATURE:
<221> NAME/KEY: misc_feature
<222> LOCATION: (12)..(12)
<223> OTHER INFORMATION: Xaa can be L, H, or F

<400> SEQUENCE: 44

Xaa Ser Asp Ile Phe Xaa Gly Glu Pro Xaa Leu Xaa Pro
1               5                   10

<210> SEQ ID NO 45
<211> LENGTH: 13
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (5)..(5)
<223> OTHER INFORMATION: Xaa can be T or K
<220> FEATURE:
<221> NAME/KEY: misc_feature
<222> LOCATION: (9)..(9)
<223> OTHER INFORMATION: Xaa can be S, P, or A
<220> FEATURE:
<221> NAME/KEY: misc_feature
<222> LOCATION: (11)..(11)
<223> OTHER INFORMATION: Xaa can be L, H, or F
<220> FEATURE:
<221> NAME/KEY: misc_feature
<222> LOCATION: (13)..(13)
<223> OTHER INFORMATION: Xaa can be D or N

<400> SEQUENCE: 45

Ser Asp Ile Phe Xaa Gly Glu Pro Xaa Leu Xaa Pro Xaa
1               5                   10

<210> SEQ ID NO 46
<211> LENGTH: 13
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (4)..(4)
<223> OTHER INFORMATION: Xaa can be T or K
<220> FEATURE:
<221> NAME/KEY: misc_feature
<222> LOCATION: (8)..(8)
<223> OTHER INFORMATION: Xaa can be S, P, or A
<220> FEATURE:
<221> NAME/KEY: misc_feature
<222> LOCATION: (10)..(10)
<223> OTHER INFORMATION: Xaa can be L, H, or F
<220> FEATURE:
<221> NAME/KEY: misc_feature
<222> LOCATION: (12)..(12)
<223> OTHER INFORMATION: Xaa can be D or N
<220> FEATURE:
<221> NAME/KEY: misc_feature
<222> LOCATION: (13)..(13)
<223> OTHER INFORMATION: Xaa can be G, S, or D
```

<400> SEQUENCE: 46

Asp Ile Phe Xaa Gly Glu Pro Xaa Leu Xaa Pro Xaa Xaa
1               5                   10

<210> SEQ ID NO 47
<211> LENGTH: 13
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (3)..(3)
<223> OTHER INFORMATION: Xaa can be T or K
<220> FEATURE:
<221> NAME/KEY: misc_feature
<222> LOCATION: (7)..(7)
<223> OTHER INFORMATION: Xaa can be S, P, or A
<220> FEATURE:
<221> NAME/KEY: misc_feature
<222> LOCATION: (9)..(9)
<223> OTHER INFORMATION: Xaa can be L, H, or F
<220> FEATURE:
<221> NAME/KEY: misc_feature
<222> LOCATION: (11)..(11)
<223> OTHER INFORMATION: Xaa can be D or N
<220> FEATURE:
<221> NAME/KEY: misc_feature
<222> LOCATION: (12)..(12)
<223> OTHER INFORMATION: Xaa can be G, S, or D
<220> FEATURE:
<221> NAME/KEY: misc_feature
<222> LOCATION: (13)..(13)
<223> OTHER INFORMATION: Xaa can be P or S

<400> SEQUENCE: 47

Ile Phe Xaa Gly Glu Pro Xaa Leu Xaa Pro Xaa Xaa Xaa
1               5                   10

<210> SEQ ID NO 48
<211> LENGTH: 13
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (2)..(2)
<223> OTHER INFORMATION: Xaa can be T or K
<220> FEATURE:
<221> NAME/KEY: misc_feature
<222> LOCATION: (6)..(6)
<223> OTHER INFORMATION: Xaa can be S, P, or A
<220> FEATURE:
<221> NAME/KEY: misc_feature
<222> LOCATION: (8)..(8)
<223> OTHER INFORMATION: Xaa can be L, H, or F
<220> FEATURE:
<221> NAME/KEY: misc_feature
<222> LOCATION: (10)..(10)
<223> OTHER INFORMATION: Xaa can be D or N
<220> FEATURE:
<221> NAME/KEY: misc_feature
<222> LOCATION: (11)..(11)
<223> OTHER INFORMATION: Xaa can be G, S, or D
<220> FEATURE:
<221> NAME/KEY: misc_feature
<222> LOCATION: (12)..(12)
<223> OTHER INFORMATION: Xaa can be P or S
<220> FEATURE:
<221> NAME/KEY: misc_feature
<222> LOCATION: (13)..(13)
<223> OTHER INFORMATION: Xaa can be V or M

```
<400> SEQUENCE: 48

Phe Xaa Gly Glu Pro Xaa Leu Xaa Pro Xaa Xaa Xaa Xaa
1               5                   10

-continued

```
<222> LOCATION: (11)..(11)
<223> OTHER INFORMATION: Xaa can be V or M
<220> FEATURE:
<221> NAME/KEY: misc_feature
<222> LOCATION: (12)..(12)
<223> OTHER INFORMATION: Xaa can be G, D, S, E, or A

<400> SEQUENCE: 50

Gly Glu Pro Xaa Leu Xaa Pro Xaa Xaa Xaa Xaa Xaa Gln
1               5                   10

<210> SEQ ID NO 51
<211> LENGTH: 13
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (3)..(3)
<223> OTHER INFORMATION: Xaa can be S, P, or A
<220> FEATURE:
<221> NAME/KEY: misc_feature
<222> LOCATION: (5)..(5)
<223> OTHER INFORMATION: Xaa can be L, H, or F
<220> FEATURE:
<221> NAME/KEY: misc_feature
<222> LOCATION: (7)..(7)
<223> OTHER INFORMATION: Xaa can be D or N
<220> FEATURE:
<221> NAME/KEY: misc_feature
<222> LOCATION: (8)..(8)
<223> OTHER INFORMATION: Xaa can be G, S, or D
<220> FEATURE:
<221> NAME/KEY: misc_feature
<222> LOCATION: (9)..(9)
<223> OTHER INFORMATION: Xaa can be P or S
<220> FEATURE:
<221> NAME/KEY: misc_feature
<222> LOCATION: (10)..(10)
<223> OTHER INFORMATION: Xaa can be V or M
<220> FEATURE:
<221> NAME/KEY: misc_feature
<222> LOCATION: (11)..(11)
<223> OTHER INFORMATION: Xaa can be G, D, S, E, or A

<400> SEQUENCE: 51

Glu Pro Xaa Leu Xaa Pro Xaa Xaa Xaa Xaa Xaa Gln Leu
1               5                   10

<210> SEQ ID NO 52
<211> LENGTH: 14
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (1)..(1)
<223> OTHER INFORMATION: Xaa can be G, D, or A
<220> FEATURE:
<221> NAME/KEY: misc_feature
<222> LOCATION: (6)..(6)
<223> OTHER INFORMATION: Xaa can be T or K
<220> FEATURE:
<221> NAME/KEY: misc_feature
<222> LOCATION: (10)..(10)
<223> OTHER INFORMATION: Xaa can be S, P, or A
<220> FEATURE:
<221> NAME/KEY: misc_feature
<222> LOCATION: (12)..(12)
<223> OTHER INFORMATION: Xaa can be L, H, or F
<220> FEATURE:
<221> NAME/KEY: misc_feature
<222> LOCATION: (14)..(14)
```

<223> OTHER INFORMATION: Xaa can be D or N

<400> SEQUENCE: 52

Xaa Ser Asp Ile Phe Xaa Gly Glu Pro Xaa Leu Xaa Pro Xaa
1               5                   10

<210> SEQ ID NO 53
<211> LENGTH: 14
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (5)..(5)
<223> OTHER INFORMATION: Xaa can be T or K
<220> FEATURE:
<221> NAME/KEY: misc_feature
<222> LOCATION: (9)..(9)
<223> OTHER INFORMATION: Xaa can be S, P, or A
<220> FEATURE:
<221> NAME/KEY: misc_feature
<222> LOCATION: (11)..(11)
<223> OTHER INFORMATION: Xaa can be L, H, or F
<220> FEATURE:
<221> NAME/KEY: misc_feature
<222> LOCATION: (13)..(13)
<223> OTHER INFORMATION: Xaa can be D or N
<220> FEATURE:
<221> NAME/KEY: misc_feature
<222> LOCATION: (14)..(14)
<223> OTHER INFORMATION: Xaa can be G, S, or D

<400> SEQUENCE: 53

Ser Asp Ile Phe Xaa Gly Glu Pro Xaa Leu Xaa Pro Xaa Xaa
1               5                   10

<210> SEQ ID NO 54
<211> LENGTH: 14
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (4)..(4)
<223> OTHER INFORMATION: Xaa can be T or K
<220> FEATURE:
<221> NAME/KEY: misc_feature
<222> LOCATION: (8)..(8)
<223> OTHER INFORMATION: Xaa can be S, P, or A
<220> FEATURE:
<221> NAME/KEY: misc_feature
<222> LOCATION: (10)..(10)
<223> OTHER INFORMATION: Xaa can be L, H, or F
<220> FEATURE:
<221> NAME/KEY: misc_feature
<222> LOCATION: (12)..(12)
<223> OTHER INFORMATION: Xaa can be D or N
<220> FEATURE:
<221> NAME/KEY: misc_feature
<222> LOCATION: (13)..(13)
<223> OTHER INFORMATION: Xaa can be G, S, or D
<220> FEATURE:
<221> NAME/KEY: misc_feature
<222> LOCATION: (14)..(14)
<223> OTHER INFORMATION: Xaa can be P or S

<400> SEQUENCE: 54

Asp Ile Phe Xaa Gly Glu Pro Xaa Leu Xaa Pro Xaa Xaa Xaa
1               5                   10

<210> SEQ ID NO 55

-continued

```
<211> LENGTH: 14
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (3)..(3)
<223> OTHER INFORMATION: Xaa can be T or K
<220> FEATURE:
<221> NAME/KEY: misc_feature
<222> LOCATION: (7)..(7)
<223> OTHER INFORMATION: Xaa can be S, P, or A
<220> FEATURE:
<221> NAME/KEY: misc_feature
<222> LOCATION: (9)..(9)
<223> OTHER INFORMATION: Xaa can be L, H, or F
<220> FEATURE:
<221> NAME/KEY: misc_feature
<222> LOCATION: (11)..(11)
<223> OTHER INFORMATION: Xaa can be D or N
<220> FEATURE:
<221> NAME/KEY: misc_feature
<222> LOCATION: (12)..(12)
<223> OTHER INFORMATION: Xaa can be G, S, or D
<220> FEATURE:
<221> NAME/KEY: misc_feature
<222> LOCATION: (13)..(13)
<223> OTHER INFORMATION: Xaa can be P or S
<220> FEATURE:
<221> NAME/KEY: misc_feature
<222> LOCATION: (14)..(14)
<223> OTHER INFORMATION: Xaa can be V or M

<400> SEQUENCE: 55

Ile Phe Xaa Gly Glu Pro Xaa Leu Xaa Pro Xaa Xaa Xaa Xaa
1               5                   10

<210> SEQ ID NO 56
<211> LENGTH: 14
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (2)..(2)
<223> OTHER INFORMATION: Xaa can be T or K
<220> FEATURE:
<221> NAME/KEY: misc_feature
<222> LOCATION: (6)..(6)
<223> OTHER INFORMATION: Xaa can be S, P, or A
<220> FEATURE:
<221> NAME/KEY: misc_feature
<222> LOCATION: (8)..(8)
<223> OTHER INFORMATION: Xaa can be L, H, or F
<220> FEATURE:
<221> NAME/KEY: misc_feature
<222> LOCATION: (10)..(10)
<223> OTHER INFORMATION: Xaa can be D or N
<220> FEATURE:
<221> NAME/KEY: misc_feature
<222> LOCATION: (11)..(11)
<223> OTHER INFORMATION: Xaa can be G, S, or D
<220> FEATURE:
<221> NAME/KEY: misc_feature
<222> LOCATION: (12)..(12)
<223> OTHER INFORMATION: Xaa can be P or S
<220> FEATURE:
<221> NAME/KEY: misc_feature
<222> LOCATION: (13)..(13)
<223> OTHER INFORMATION: Xaa can be V or M
<220> FEATURE:
<221> NAME/KEY: misc_feature
<222> LOCATION: (14)..(14)
<223> OTHER INFORMATION: Xaa can be G, D, S, E, or A
```

-continued

```
<400> SEQUENCE: 56

Phe Xaa Gly Glu Pro Xaa Leu Xaa Pro Xaa Xaa Xaa Xaa Xaa
1               5                   10

<210> SEQ ID NO 57
<211> LENGTH: 14
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (1)..(1)
<223> OTHER INFORMATION: Xaa can be T or K
<220> FEATURE:
<221> NAME/KEY: misc_feature
<222> LOCATION: (5)..(5)
<223> OTHER INFORMATION: Xaa can be S, P, or A
<220> FEATURE:
<221> NAME/KEY: misc_feature
<222> LOCATION: (7)..(7)
<223> OTHER INFORMATION: Xaa can be L, H, or F
<220> FEATURE:
<221> NAME/KEY: misc_feature
<222> LOCATION: (9)..(9)
<223> OTHER INFORMATION: Xaa can be D or N
<220> FEATURE:
<221> NAME/KEY: misc_feature
<222> LOCATION: (10)..(10)
<223> OTHER INFORMATION: Xaa can be G, S, or D
<220> FEATURE:
<221> NAME/KEY: misc_feature
<222> LOCATION: (11)..(11)
<223> OTHER INFORMATION: Xaa can be P or S
<220> FEATURE:
<221> NAME/KEY: misc_feature
<222> LOCATION: (12)..(12)
<223> OTHER INFORMATION: Xaa can be V or M
<220> FEATURE:
<221> NAME/KEY: misc_feature
<222> LOCATION: (13)..(13)
<223> OTHER INFORMATION: Xaa can be G, D, S, E, or A

<400> SEQUENCE: 57

Xaa Gly Glu Pro Xaa Leu Xaa Pro Xaa Xaa Xaa Xaa Xaa Gln
1               5                   10

<210> SEQ ID NO 58
<211> LENGTH: 14
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (4)..(4)
<223> OTHER INFORMATION: Xaa can be S, P, or A
<220> FEATURE:
<221> NAME/KEY: misc_feature
<222> LOCATION: (6)..(6)
<223> OTHER INFORMATION: Xaa can be L, H, or F
<220> FEATURE:
<221> NAME/KEY: misc_feature
<222> LOCATION: (8)..(8)
<223> OTHER INFORMATION: Xaa can be D or N
<220> FEATURE:
<221> NAME/KEY: misc_feature
<222> LOCATION: (9)..(9)
<223> OTHER INFORMATION: Xaa can be G, S, or D
<220> FEATURE:
<221> NAME/KEY: misc_feature
<222> LOCATION: (10)..(10)
<223> OTHER INFORMATION: Xaa can be P or S
<220> FEATURE:
<221> NAME/KEY: misc_feature
```

-continued

```
<222> LOCATION: (11)..(11)
<223> OTHER INFORMATION: Xaa can be V or M
<220> FEATURE:
<221> NAME/KEY: misc_feature
<222> LOCATION: (12)..(12)
<223> OTHER INFORMATION: Xaa can be G, D, S, E, or A

<400> SEQUENCE: 58

Gly Glu Pro Xaa Leu Xaa Pro Xaa Xaa Xaa Xaa Xaa Gln Leu
1               5                   10

<210> SEQ ID NO 59
<211> LENGTH: 15
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (1)..(1)
<223> OTHER INFORMATION: Xaa can be G, D, or A
<220> FEATURE:
<221> NAME/KEY: misc_feature
<222> LOCATION: (6)..(6)
<223> OTHER INFORMATION: Xaa can be T or K
<220> FEATURE:
<221> NAME/KEY: misc_feature
<222> LOCATION: (10)..(10)
<223> OTHER INFORMATION: Xaa can be S, P, or A
<220> FEATURE:
<221> NAME/KEY: misc_feature
<222> LOCATION: (12)..(12)
<223> OTHER INFORMATION: Xaa can be L, H, or F
<220> FEATURE:
<221> NAME/KEY: misc_feature
<222> LOCATION: (14)..(14)
<223> OTHER INFORMATION: Xaa can be D or N
<220> FEATURE:
<221> NAME/KEY: misc_feature
<222> LOCATION: (15)..(15)
<223> OTHER INFORMATION: Xaa can be G, S, or D

<400> SEQUENCE: 59

Xaa Ser Asp Ile Phe Xaa Gly Glu Pro Xaa Leu Xaa Pro Xaa Xaa
1               5                   10                  15

<210> SEQ ID NO 60
<211> LENGTH: 15
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (5)..(5)
<223> OTHER INFORMATION: Xaa can be T or K
<220> FEATURE:
<221> NAME/KEY: misc_feature
<222> LOCATION: (9)..(9)
<223> OTHER INFORMATION: Xaa can be S, P, or A
<220> FEATURE:
<221> NAME/KEY: misc_feature
<222> LOCATION: (11)..(11)
<223> OTHER INFORMATION: Xaa can be L, H, or F
<220> FEATURE:
<221> NAME/KEY: misc_feature
<222> LOCATION: (13)..(13)
<223> OTHER INFORMATION: Xaa can be D or N
<220> FEATURE:
<221> NAME/KEY: misc_feature
<222> LOCATION: (14)..(14)
<223> OTHER INFORMATION: Xaa can be G, S, or D
<220> FEATURE:
<221> NAME/KEY: misc_feature
<222> LOCATION: (15)..(15)
```

<223> OTHER INFORMATION: Xaa can be P or S

<400> SEQUENCE: 60

Ser Asp Ile Phe Xaa Gly Glu Pro Xaa Leu Xaa Pro Xaa Xaa Xaa
1               5                   10                  15

<210> SEQ ID NO 61
<211> LENGTH: 15
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (4)..(4)
<223> OTHER INFORMATION: Xaa can be T or K
<220> FEATURE:
<221> NAME/KEY: misc_feature
<222> LOCATION: (8)..(8)
<223> OTHER INFORMATION: Xaa can be S, P, or A
<220> FEATURE:
<221> NAME/KEY: misc_feature
<222> LOCATION: (10)..(10)
<223> OTHER INFORMATION: Xaa can be L, H, or F
<220> FEATURE:
<221> NAME/KEY: misc_feature
<222> LOCATION: (12)..(12)
<223> OTHER INFORMATION: Xaa can be D or N
<220> FEATURE:
<221> NAME/KEY: misc_feature
<222> LOCATION: (13)..(13)
<223> OTHER INFORMATION: Xaa can be G, S, or D
<220> FEATURE:
<221> NAME/KEY: misc_feature
<222> LOCATION: (14)..(14)
<223> OTHER INFORMATION: Xaa can be P or S
<220> FEATURE:
<221> NAME/KEY: misc_feature
<222> LOCATION: (15)..(15)
<223> OTHER INFORMATION: Xaa can be V or M

<400> SEQUENCE: 61

Asp Ile Phe Xaa Gly Glu Pro Xaa Leu Xaa Pro Xaa Xaa Xaa Xaa
1               5                   10                  15

<210> SEQ ID NO 62
<211> LENGTH: 15
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (3)..(3)
<223> OTHER INFORMATION: Xaa can be T or K
<220> FEATURE:
<221> NAME/KEY: misc_feature
<222> LOCATION: (7)..(7)
<223> OTHER INFORMATION: Xaa can be S, P, or A
<220> FEATURE:
<221> NAME/KEY: misc_feature
<222> LOCATION: (9)..(9)
<223> OTHER INFORMATION: Xaa can be L, H, or F
<220> FEATURE:
<221> NAME/KEY: misc_feature
<222> LOCATION: (11)..(11)
<223> OTHER INFORMATION: Xaa can be D or N
<220> FEATURE:
<221> NAME/KEY: misc_feature
<222> LOCATION: (12)..(12)
<223> OTHER INFORMATION: Xaa can be G, S, or D
<220> FEATURE:
<221> NAME/KEY: misc_feature
<222> LOCATION: (13)..(13)
<223> OTHER INFORMATION: Xaa can be P or S

```
<220> FEATURE:
<221> NAME/KEY: misc_feature
<222> LOCATION: (14)..(14)
<223> OTHER INFORMATION: Xaa can be V or M
<220> FEATURE:
<221> NAME/KEY: misc_feature
<222> LOCATION: (15)..(15)
<223> OTHER INFORMATION: Xaa can be G, D, S, E, or A

<400> SEQUENCE: 62

Ile Phe Xaa Gly Glu Pro Xaa Leu Xaa Pro Xaa Xaa Xaa Xaa Xaa
1               5                   10                  15

<210> SEQ ID NO 63
<211> LENGTH: 15
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (2)..(2)
<223> OTHER INFORMATION: Xaa can be T or K
<220> FEATURE:
<221> NAME/KEY: misc_feature
<222> LOCATION: (6)..(6)
<223> OTHER INFORMATION: Xaa can be S, P, or A
<220> FEATURE:
<221> NAME/KEY: misc_feature
<222> LOCATION: (8)..(8)
<223> OTHER INFORMATION: Xaa can be L, H, or F
<220> FEATURE:
<221> NAME/KEY: misc_feature
<222> LOCATION: (10)..(10)
<223> OTHER INFORMATION: Xaa can be D or N
<220> FEATURE:
<221> NAME/KEY: misc_feature
<222> LOCATION: (11)..(11)
<223> OTHER INFORMATION: Xaa can be G, S, or D
<220> FEATURE:
<221> NAME/KEY: misc_feature
<222> LOCATION: (12)..(12)
<223> OTHER INFORMATION: Xaa can be P or S
<220> FEATURE:
<221> NAME/KEY: misc_feature
<222> LOCATION: (13)..(13)
<223> OTHER INFORMATION: Xaa can be V or M
<220> FEATURE:
<221> NAME/KEY: misc_feature
<222> LOCATION: (14)..(14)
<223> OTHER INFORMATION: Xaa can be G, D, S, E, or A

<400> SEQUENCE: 63

Phe Xaa Gly Glu Pro Xaa Leu Xaa Pro Xaa Xaa Xaa Xaa Xaa Gln
1               5                   10                  15

<210> SEQ ID NO 64
<211> LENGTH: 15
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (1)..(1)
<223> OTHER INFORMATION: Xaa can be T or K
<220> FEATURE:
<221> NAME/KEY: misc_feature
<222> LOCATION: (5)..(5)
<223> OTHER INFORMATION: Xaa can be S, P, or A
<220> FEATURE:
<221> NAME/KEY: misc_feature
<222> LOCATION: (7)..(7)
<223> OTHER INFORMATION: Xaa can be L, H, or F
<220> FEATURE:
```

```
<221> NAME/KEY: misc_feature
<222> LOCATION: (9)..(9)
<223> OTHER INFORMATION: Xaa can be D or N
<220> FEATURE:
<221> NAME/KEY: misc_feature
<222> LOCATION: (10)..(10)
<223> OTHER INFORMATION: Xaa can be G, S, or D
<220> FEATURE:
<221> NAME/KEY: misc_feature
<222> LOCATION: (11)..(11)
<223> OTHER INFORMATION: Xaa can be P or S
<220> FEATURE:
<221> NAME/KEY: misc_feature
<222> LOCATION: (12)..(12)
<223> OTHER INFORMATION: Xaa can be V or M
<220> FEATURE:
<221> NAME/KEY: misc_feature
<222> LOCATION: (13)..(13)
<223> OTHER INFORMATION: Xaa can be G, D, S, E, or A

<400> SEQUENCE: 64

Xaa Gly Glu Pro Xaa Leu Xaa Pro Xaa Xaa Xaa Xaa Xaa Gln Leu
1               5                  10                  15

<210> SEQ ID NO 65
<211> LENGTH: 16
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (1)..(1)
<223> OTHER INFORMATION: Xaa can be G, D, or A
<220> FEATURE:
<221> NAME/KEY: misc_feature
<222> LOCATION: (6)..(6)
<223> OTHER INFORMATION: Xaa can be T or K
<220> FEATURE:
<221> NAME/KEY: misc_feature
<222> LOCATION: (10)..(10)
<223> OTHER INFORMATION: Xaa can be S, P, or A
<220> FEATURE:
<221> NAME/KEY: misc_feature
<222> LOCATION: (12)..(12)
<223> OTHER INFORMATION: Xaa can be L, H, or F
<220> FEATURE:
<221> NAME/KEY: misc_feature
<222> LOCATION: (14)..(14)
<223> OTHER INFORMATION: Xaa can be D or N
<220> FEATURE:
<221> NAME/KEY: misc_feature
<222> LOCATION: (15)..(15)
<223> OTHER INFORMATION: Xaa can be G, S, or D
<220> FEATURE:
<221> NAME/KEY: misc_feature
<222> LOCATION: (16)..(16)
<223> OTHER INFORMATION: Xaa can be P or S

<400> SEQUENCE: 65

Xaa Ser Asp Ile Phe Xaa Gly Glu Pro Xaa Leu Xaa Pro Xaa Xaa Xaa
1               5                  10                  15

<210> SEQ ID NO 66
<211> LENGTH: 16
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (5)..(5)
<223> OTHER INFORMATION: Xaa can be T or K
<220> FEATURE:
<221> NAME/KEY: misc_feature
```

```
<222> LOCATION: (9)..(9)
<223> OTHER INFORMATION: Xaa can be S, P, or A
<220> FEATURE:
<221> NAME/KEY: misc_feature
<222> LOCATION: (11)..(11)
<223> OTHER INFORMATION: Xaa can be L, H, or F
<220> FEATURE:
<221> NAME/KEY: misc_feature
<222> LOCATION: (13)..(13)
<223> OTHER INFORMATION: Xaa can be D or N
<220> FEATURE:
<221> NAME/KEY: misc_feature
<222> LOCATION: (14)..(14)
<223> OTHER INFORMATION: Xaa can be G, S, or D
<220> FEATURE:
<221> NAME/KEY: misc_feature
<222> LOCATION: (15)..(15)
<223> OTHER INFORMATION: Xaa can be P or S
<220> FEATURE:
<221> NAME/KEY: misc_feature
<222> LOCATION: (16)..(16)
<223> OTHER INFORMATION: Xaa can be V or M

<400> SEQUENCE: 66

Ser Asp Ile Phe Xaa Gly Glu Pro Xaa Leu Xaa Pro Xaa Xaa Xaa Xaa
1               5                   10                  15

<210> SEQ ID NO 67
<211> LENGTH: 16
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (4)..(4)
<223> OTHER INFORMATION: Xaa can be T or K
<220> FEATURE:
<221> NAME/KEY: misc_feature
<222> LOCATION: (8)..(8)
<223> OTHER INFORMATION: Xaa can be S, P, or A
<220> FEATURE:
<221> NAME/KEY: misc_feature
<222> LOCATION: (10)..(10)
<223> OTHER INFORMATION: Xaa can be L, H, or F
<220> FEATURE:
<221> NAME/KEY: misc_feature
<222> LOCATION: (12)..(12)
<223> OTHER INFORMATION: Xaa can be D or N
<220> FEATURE:
<221> NAME/KEY: misc_feature
<222> LOCATION: (13)..(13)
<223> OTHER INFORMATION: Xaa can be G, S, or D
<220> FEATURE:
<221> NAME/KEY: misc_feature
<222> LOCATION: (14)..(14)
<223> OTHER INFORMATION: Xaa can be P or S
<220> FEATURE:
<221> NAME/KEY: misc_feature
<222> LOCATION: (15)..(15)
<223> OTHER INFORMATION: Xaa can be V or M
<220> FEATURE:
<221> NAME/KEY: misc_feature
<222> LOCATION: (16)..(16)
<223> OTHER INFORMATION: Xaa can be G, D, S, E, or A

<400> SEQUENCE: 67

Asp Ile Phe Xaa Gly Glu Pro Xaa Leu Xaa Pro Xaa Xaa Xaa Xaa Xaa
1               5                   10                  15

<210> SEQ ID NO 68
<211> LENGTH: 16
<212> TYPE: PRT
<213> ORGANISM: Artificial sequence
<220> FEATURE:
```

```
<223> OTHER INFORMATION: IL-23p19 fragment
<220> FEATURE:
<221> NAME/KEY: misc_feature
<222> LOCATION: (3)..(3)
<223> OTHER INFORMATION: Xaa can be T or K
<220> FEATURE:
<221> NAME/KEY: misc_feature
<222> LOCATION: (7)..(7)
<223> OTHER INFORMATION: Xaa can be S, P, or A
<220> FEATURE:
<221> NAME/KEY: misc_feature
<222> LOCATION: (9)..(9)
<223> OTHER INFORMATION: Xaa can be L, H, or F
<220> FEATURE:
<221> NAME/KEY: misc_feature
<222> LOCATION: (11)..(11)
<223> OTHER INFORMATION: Xaa can be D or N
<220> FEATURE:
<221> NAME/KEY: misc_feature
<222> LOCATION: (12)..(12)
<223> OTHER INFORMATION: Xaa can be G, S, or D
<220> FEATURE:
<221> NAME/KEY: misc_feature
<222> LOCATION: (13)..(13)
<223> OTHER INFORMATION: Xaa can be P or S
<220> FEATURE:
<221> NAME/KEY: misc_feature
<222> LOCATION: (14)..(14)
<223> OTHER INFORMATION: Xaa can be V or M
<220> FEATURE:
<221> NAME/KEY: misc_feature
<222> LOCATION: (15)..(15)
<223> OTHER INFORMATION: Xaa can be G, D, S, E, or A

<400> SEQUENCE: 68

Ile Phe Xaa Gly Glu Pro Xaa Leu Xaa Pro Xaa Xaa Xaa Xaa Xaa Gln
1               5                   10                  15

<210> SEQ ID NO 69
<211> LENGTH: 16
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (2)..(2)
<223> OTHER INFORMATION: Xaa can be T or K
<220> FEATURE:
<221> NAME/KEY: misc_feature
<222> LOCATION: (6)..(6)
<223> OTHER INFORMATION: Xaa can be S, P, or A
<220> FEATURE:
<221> NAME/KEY: misc_feature
<222> LOCATION: (8)..(8)
<223> OTHER INFORMATION: Xaa can be L, H, or F
<220> FEATURE:
<221> NAME/KEY: misc_feature
<222> LOCATION: (10)..(10)
<223> OTHER INFORMATION: Xaa can be D or N
<220> FEATURE:
<221> NAME/KEY: misc_feature
<222> LOCATION: (11)..(11)
<223> OTHER INFORMATION: Xaa can be G, S, or D
<220> FEATURE:
<221> NAME/KEY: misc_feature
<222> LOCATION: (12)..(12)
<223> OTHER INFORMATION: Xaa can be P or S
<220> FEATURE:
<221> NAME/KEY: misc_feature
<222> LOCATION: (13)..(13)
<223> OTHER INFORMATION: Xaa can be V or M
<220> FEATURE:
<221> NAME/KEY: misc_feature
<222> LOCATION: (14)..(14)
<223> OTHER INFORMATION: Xaa can be G, D, S, E, or A
```

<400> SEQUENCE: 69

Phe Xaa Gly Glu Pro Xaa Leu Xaa Pro Xaa Xaa Xaa Xaa Xaa Gln Leu
1               5                   10                  15

<210> SEQ ID NO 70
<211> LENGTH: 17
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (1)..(1)
<223> OTHER INFORMATION: Xaa can be G, D, or A
<220> FEATURE:
<221> NAME/KEY: misc_feature
<222> LOCATION: (6)..(6)
<223> OTHER INFORMATION: Xaa can be T or K
<220> FEATURE:
<221> NAME/KEY: misc_feature
<222> LOCATION: (10)..(10)
<223> OTHER INFORMATION: Xaa can be S, P, or A
<220> FEATURE:
<221> NAME/KEY: misc_feature
<222> LOCATION: (12)..(12)
<223> OTHER INFORMATION: Xaa can be L, H, or F
<220> FEATURE:
<221> NAME/KEY: misc_feature
<222> LOCATION: (14)..(14)
<223> OTHER INFORMATION: Xaa can be D or N
<220> FEATURE:
<221> NAME/KEY: misc_feature
<222> LOCATION: (15)..(15)
<223> OTHER INFORMATION: Xaa can be G, S, or D
<220> FEATURE:
<221> NAME/KEY: misc_feature
<222> LOCATION: (16)..(16)
<223> OTHER INFORMATION: Xaa can be P or S
<220> FEATURE:
<221> NAME/KEY: misc_feature
<222> LOCATION: (17)..(17)
<223> OTHER INFORMATION: Xaa can be V or M

<400> SEQUENCE: 70

Xaa Ser Asp Ile Phe Xaa Gly Glu Pro Xaa Leu Xaa Pro Xaa Xaa Xaa
1               5                   10                  15

Xaa

<210> SEQ ID NO 71
<211> LENGTH: 17
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (5)..(5)
<223> OTHER INFORMATION: Xaa can be T or K
<220> FEATURE:
<221> NAME/KEY: misc_feature
<222> LOCATION: (9)..(9)
<223> OTHER INFORMATION: Xaa can be S, P, or A
<220> FEATURE:
<221> NAME/KEY: misc_feature
<222> LOCATION: (11)..(11)
<223> OTHER INFORMATION: Xaa can be L, H, or F
<220> FEATURE:
<221> NAME/KEY: misc_feature
<222> LOCATION: (13)..(13)
<223> OTHER INFORMATION: Xaa can be D or N
<220> FEATURE:
<221> NAME/KEY: misc_feature
<222> LOCATION: (14)..(14)
<223> OTHER INFORMATION: Xaa can be G, S, or D -continued

```
<220> FEATURE:
<221> NAME/KEY: misc_feature
<222> LOCATION: (15)..(15)
<223> OTHER INFORMATION: Xaa can be P or S
<220> FEATURE:
<221> NAME/KEY: misc_feature
<222> LOCATION: (16)..(16)
<223> OTHER INFORMATION: Xaa can be V or M
<220> FEATURE:
<221> NAME/KEY: misc_feature
<222> LOCATION: (17)..(17)
<223> OTHER INFORMATION: Xaa can be G, D, S, E, or A

<400> SEQUENCE: 71

Ser Asp Ile Phe Xaa Gly Glu Pro Xaa Leu Xaa Pro Xaa Xaa Xaa Xaa
1               5                   10                  15

Xaa

<210> SEQ ID NO 72
<211> LENGTH: 17
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (4)..(4)
<223> OTHER INFORMATION: Xaa can be T or K
<220> FEATURE:
<221> NAME/KEY: misc_feature
<222> LOCATION: (8)..(8)
<223> OTHER INFORMATION: Xaa can be S, P, or A
<220> FEATURE:
<221> NAME/KEY: misc_feature
<222> LOCATION: (10)..(10)
<223> OTHER INFORMATION: Xaa can be L, H, or F
<220> FEATURE:
<221> NAME/KEY: misc_feature
<222> LOCATION: (12)..(12)
<223> OTHER INFORMATION: Xaa can be D or N
<220> FEATURE:
<221> NAME/KEY: misc_feature
<222> LOCATION: (13)..(13)
<223> OTHER INFORMATION: Xaa can be G, S, or D
<220> FEATURE:
<221> NAME/KEY: misc_feature
<222> LOCATION: (14)..(14)
<223> OTHER INFORMATION: Xaa can be P or S
<220> FEATURE:
<221> NAME/KEY: misc_feature
<222> LOCATION: (15)..(15)
<223> OTHER INFORMATION: Xaa can be V or M
<220> FEATURE:
<221> NAME/KEY: misc_feature
<222> LOCATION: (16)..(16)
<223> OTHER INFORMATION: Xaa can be G, D, S, E, or A

<400> SEQUENCE: 72

Asp Ile Phe Xaa Gly Glu Pro Xaa Leu Xaa Pro Xaa Xaa Xaa Xaa Xaa
1               5                   10                  15

Gln

<210> SEQ ID NO 73
<211> LENGTH: 17
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (3)..(3)
<223> OTHER INFORMATION: Xaa can be T or K
<220> FEATURE:
```

-continued

```
<221> NAME/KEY: misc_feature
<222> LOCATION: (7)..(7)
<223> OTHER INFORMATION: Xaa can be S, P, or A
<220> FEATURE:
<221> NAME/KEY: misc_feature
<222> LOCATION: (9)..(9)
<223> OTHER INFORMATION: Xaa can be L, H, or F
<220> FEATURE:
<221> NAME/KEY: misc_feature
<222> LOCATION: (11)..(11)
<223> OTHER INFORMATION: Xaa can be D or N
<220> FEATURE:
<221> NAME/KEY: misc_feature
<222> LOCATION: (12)..(12)
<223> OTHER INFORMATION: Xaa can be G, S, or D
<220> FEATURE:
<221> NAME/KEY: misc_feature
<222> LOCATION: (13)..(13)
<223> OTHER INFORMATION: Xaa can be P or S
<220> FEATURE:
<221> NAME/KEY: misc_feature
<222> LOCATION: (14)..(14)
<223> OTHER INFORMATION: Xaa can be V or M
<220> FEATURE:
<221> NAME/KEY: misc_feature
<222> LOCATION: (15)..(15)
<223> OTHER INFORMATION: Xaa can be G, D, S, E, or A

<400> SEQUENCE: 73

Ile Phe Xaa Gly Glu Pro Xaa Leu Xaa Pro Xaa Xaa Xaa Xaa Xaa Gln
1               5                   10                  15

Leu

<210> SEQ ID NO 74
<211> LENGTH: 18
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (1)..(1)
<223> OTHER INFORMATION: Xaa can be G, D, or A
<220> FEATURE:
<221> NAME/KEY: misc_feature
<222> LOCATION: (6)..(6)
<223> OTHER INFORMATION: Xaa can be T or K
<220> FEATURE:
<221> NAME/KEY: misc_feature
<222> LOCATION: (10)..(10)
<223> OTHER INFORMATION: Xaa can be S, P, or A
<220> FEATURE:
<221> NAME/KEY: misc_feature
<222> LOCATION: (12)..(12)
<223> OTHER INFORMATION: Xaa can be L, H, or F
<220> FEATURE:
<221> NAME/KEY: misc_feature
<222> LOCATION: (14)..(14)
<223> OTHER INFORMATION: Xaa can be D or N
<220> FEATURE:
<221> NAME/KEY: misc_feature
<222> LOCATION: (15)..(15)
<223> OTHER INFORMATION: Xaa can be G, S, or D
<220> FEATURE:
<221> NAME/KEY: misc_feature
<222> LOCATION: (16)..(16)
<223> OTHER INFORMATION: Xaa can be P or S
<220> FEATURE:
<221> NAME/KEY: misc_feature
<222> LOCATION: (17)..(17)
<223> OTHER INFORMATION: Xaa can be V or M
<220> FEATURE:
<221> NAME/KEY: misc_feature
<222> LOCATION: (18)..(18)
<223> OTHER INFORMATION: Xaa can be G, D, S, E, or A
```

-continued

<400> SEQUENCE: 74

Xaa Ser Asp Ile Phe Xaa Gly Glu Pro Xaa Leu Xaa Pro Xaa Xaa Xaa
1               5                   10                  15

Xaa Xaa

<210> SEQ ID NO 75
<211> LENGTH: 18
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (5)..(5)
<223> OTHER INFORMATION: Xaa can be T or K
<220> FEATURE:
<221> NAME/KEY: misc_feature
<222> LOCATION: (9)..(9)
<223> OTHER INFORMATION: Xaa can be S, P, or A
<220> FEATURE:
<221> NAME/KEY: misc_feature
<222> LOCATION: (11)..(11)
<223> OTHER INFORMATION: Xaa can be L, H, or F
<220> FEATURE:
<221> NAME/KEY: misc_feature
<222> LOCATION: (13)..(13)
<223> OTHER INFORMATION: Xaa can be D or N
<220> FEATURE:
<221> NAME/KEY: misc_feature
<222> LOCATION: (14)..(14)
<223> OTHER INFORMATION: Xaa can be G, S, or D
<220> FEATURE:
<221> NAME/KEY: misc_feature
<222> LOCATION: (15)..(15)
<223> OTHER INFORMATION: Xaa can be P or S
<220> FEATURE:
<221> NAME/KEY: misc_feature
<222> LOCATION: (16)..(16)
<223> OTHER INFORMATION: Xaa can be V or M
<220> FEATURE:
<221> NAME/KEY: misc_feature
<222> LOCATION: (17)..(17)
<223> OTHER INFORMATION: Xaa can be G, D, S, E, or A

<400> SEQUENCE: 75

Ser Asp Ile Phe Xaa Gly Glu Pro Xaa Leu Xaa Pro Xaa Xaa Xaa Xaa
1               5                   10                  15

Xaa Gln

<210> SEQ ID NO 76
<211> LENGTH: 18
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (4)..(4)
<223> OTHER INFORMATION: Xaa can be T or K
<220> FEATURE:
<221> NAME/KEY: misc_feature
<222> LOCATION: (8)..(8)
<223> OTHER INFORMATION: Xaa can be S, P, or A
<220> FEATURE:
<221> NAME/KEY: misc_feature
<222> LOCATION: (10)..(10)
<223> OTHER INFORMATION: Xaa can be L, H, or F
<220> FEATURE:
<221> NAME/KEY: misc_feature
<222> LOCATION: (12)..(12)
<223> OTHER INFORMATION: Xaa can be D or N
<220> FEATURE:
<221> NAME/KEY: misc_feature

```
<222> LOCATION: (13)..(13)
<223> OTHER INFORMATION: Xaa can be G, S, or D
<220> FEATURE:
<221> NAME/KEY: misc_feature
<222> LOCATION: (14)..(14)
<223> OTHER INFORMATION: Xaa can be P or S
<220> FEATURE:
<221> NAME/KEY: misc_feature
<222> LOCATION: (15)..(15)
<223> OTHER INFORMATION: Xaa can be V or M
<220> FEATURE:
<221> NAME/KEY: misc_feature
<222> LOCATION: (16)..(16)
<223> OTHER INFORMATION: Xaa can be G, D, S, E, or A

<400> SEQUENCE: 76

Asp Ile Phe Xaa Gly Glu Pro Xaa Leu Xaa Pro Xaa Xaa Xaa Xaa Xaa
1               5                   10                  15

Gln Leu

<210> SEQ ID NO 77
<211> LENGTH: 19
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (1)..(1)
<223> OTHER INFORMATION: Xaa can be G, D, or A
<220> FEATURE:
<221> NAME/KEY: misc_feature
<222> LOCATION: (6)..(6)
<223> OTHER INFORMATION: Xaa can be T or K
<220> FEATURE:
<221> NAME/KEY: misc_feature
<222> LOCATION: (10)..(10)
<223> OTHER INFORMATION: Xaa can be S, P, or A
<220> FEATURE:
<221> NAME/KEY: misc_feature
<222> LOCATION: (12)..(12)
<223> OTHER INFORMATION: Xaa can be L, H, or F
<220> FEATURE:
<221> NAME/KEY: misc_feature
<222> LOCATION: (14)..(14)
<223> OTHER INFORMATION: Xaa can be D or N
<220> FEATURE:
<221> NAME/KEY: misc_feature
<222> LOCATION: (15)..(15)
<223> OTHER INFORMATION: Xaa can be G, S, or D
<220> FEATURE:
<221> NAME/KEY: misc_feature
<222> LOCATION: (16)..(16)
<223> OTHER INFORMATION: Xaa can be P or S
<220> FEATURE:
<221> NAME/KEY: misc_feature
<222> LOCATION: (17)..(17)
<223> OTHER INFORMATION: Xaa can be V or M
<220> FEATURE:
<221> NAME/KEY: misc_feature
<222> LOCATION: (18)..(18)
<223> OTHER INFORMATION: Xaa can be G, D, S, E, or A

<400> SEQUENCE: 77

Xaa Ser Asp Ile Phe Xaa Gly Glu Pro Xaa Leu Xaa Pro Xaa Xaa Xaa
1               5                   10                  15

Xaa Xaa Gln

<210> SEQ ID NO 78
<211> LENGTH: 19
<212> TYPE: PRT
<213> ORGANISM: Artificial sequence
<220> FEATURE:
```

```
<223> OTHER INFORMATION: IL-23p19 fragment
<220> FEATURE:
<221> NAME/KEY: misc_feature
<222> LOCATION: (5)..(5)
<223> OTHER INFORMATION: Xaa can be T or K
<220> FEATURE:
<221> NAME/KEY: misc_feature
<222> LOCATION: (9)..(9)
<223> OTHER INFORMATION: Xaa can be S, P, or A
<220> FEATURE:
<221> NAME/KEY: misc_feature
<222> LOCATION: (11)..(11)
<223> OTHER INFORMATION: Xaa can be L, H, or F
<220> FEATURE:
<221> NAME/KEY: misc_feature
<222> LOCATION: (13)..(13)
<223> OTHER INFORMATION: Xaa can be D or N
<220> FEATURE:
<221> NAME/KEY: misc_feature
<222> LOCATION: (14)..(14)
<223> OTHER INFORMATION: Xaa can be G, S, or D
<220> FEATURE:
<221> NAME/KEY: misc_feature
<222> LOCATION: (15)..(15)
<223> OTHER INFORMATION: Xaa can be P or S
<220> FEATURE:
<221> NAME/KEY: misc_feature
<222> LOCATION: (16)..(16)
<223> OTHER INFORMATION: Xaa can be V or M
<220> FEATURE:
<221> NAME/KEY: misc_feature
<222> LOCATION: (17)..(17)
<223> OTHER INFORMATION: Xaa can be G, D, S, E, or A

<400> SEQUENCE: 78

Ser Asp Ile Phe Xaa Gly Glu Pro Xaa Leu Xaa Pro Xaa Xaa Xaa Xaa
1               5                   10                  15

Xaa Gln Leu

<210> SEQ ID NO 79
<211> LENGTH: 20
<212> TYPE: PRT
<213> ORGANISM: Artificial sequence
<220> FEATURE:
<223> OTHER INFORMATION: IL-23p19 fragment
<220> FEATURE:
<221> NAME/KEY: misc_feature
<222> LOCATION: (1)..(1)
<223> OTHER INFORMATION: Xaa can be G, D, or A
<220> FEATURE:
<221> NAME/KEY: misc_feature
<222> LOCATION: (6)..(6)
<223> OTHER INFORMATION: Xaa can be T or K
<220> FEATURE:
<221> NAME/KEY: misc_feature
<222> LOCATION: (10)..(10)
<223> OTHER INFORMATION: Xaa can be S, P, or A
<220> FEATURE:
<221> NAME/KEY: misc_feature
<222> LOCATION: (12)..(12)
<223> OTHER INFORMATION: Xaa can be L, H, or F
<220> FEATURE:
<221> NAME/KEY: misc_feature
<222> LOCATION: (14)..(14)
<223> OTHER INFORMATION: Xaa can be D or N
<220> FEATURE:
<221> NAME/KEY: misc_feature
<222> LOCATION: (15)..(15)
<223> OTHER INFORMATION: Xaa can be G, S, or D
<220> FEATURE:
<221> NAME/KEY: misc_feature
<222> LOCATION: (16)..(16)
<223> OTHER INFORMATION: Xaa can be P or S
<220> FEATURE:
<221> NAME/KEY: misc_feature
<222> LOCATION: (17)..(17)
```

<223> OTHER INFORMATION: Xaa can be V or M
<220> FEATURE:
<221> NAME/KEY: misc_feature
<222> LOCATION: (18)..(18)
<223> OTHER INFORMATION: Xaa can be G, D, S, E, or A

<400> SEQUENCE: 79

Xaa Ser Asp Ile Phe Xaa Gly Glu Pro Xaa Leu Xaa Pro Xaa Xaa Xaa
1               5                   10                  15

Xaa Xaa Gln Leu
            20

<210> SEQ ID NO 80
<211> LENGTH: 11
<212> TYPE: PRT
<213> ORGANISM: Artificial sequence
<220> FEATURE:
<223> OTHER INFORMATION: IL-23p19 fragment

<400> SEQUENCE: 80

Gly Ser Asp Ile Phe Thr Gly Glu Pro Ser Leu
1               5                   10

<210> SEQ ID NO 81
<211> LENGTH: 11
<212> TYPE: PRT
<213> ORGANISM: Artificial sequence
<220> FEATURE:
<223> OTHER INFORMATION: IL-23p19 fragment

<400> SEQUENCE: 81

Ser Asp Ile Phe Thr Gly Glu Pro Ser Leu Leu
1               5                   10

<210> SEQ ID NO 82
<211> LENGTH: 11
<212> TYPE: PRT
<213> ORGANISM: Artificial sequence
<220> FEATURE:
<223> OTHER INFORMATION: IL-23p19 fragment

<400> SEQUENCE: 82

Asp Ile Phe Thr Gly Glu Pro Ser Leu Leu Pro
1               5                   10

<210> SEQ ID NO 83
<211> LENGTH: 11
<212> TYPE: PRT
<213> ORGANISM: Artificial sequence
<220> FEATURE:
<223> OTHER INFORMATION: IL-23p19 fragment

<400> SEQUENCE: 83

Ile Phe Thr Gly Glu Pro Ser Leu Leu Pro Asp
1               5                   10

<210> SEQ ID NO 84
<211> LENGTH: 11
<212> TYPE: PRT
<213> ORGANISM: Artificial sequence
<220> FEATURE:
<223> OTHER INFORMATION: IL-23p19 fragment

<400> SEQUENCE: 84

Phe Thr Gly Glu Pro Ser Leu Leu Pro Asp Ser
1               5                   10

<210> SEQ ID NO 85
<211> LENGTH: 11
<212> TYPE: PRT
<213> ORGANISM: Artificial sequence
<220> FEATURE:
<223> OTHER INFORMATION: IL-23p19 fragment

<400> SEQUENCE: 85

Thr Gly Glu Pro Ser Leu Leu Pro Asp Ser Pro
1               5                   10

<210> SEQ ID NO 86
<211> LENGTH: 11
<212> TYPE: PRT
<213> ORGANISM: Artificial sequence
<220> FEATURE:
<223> OTHER INFORMATION: IL-23p19 fragment

<400> SEQUENCE: 86

Lys Gly Glu Pro Ser Leu Leu Pro Asp Ser Pro
1               5                   10

<210> SEQ ID NO 87
<211> LENGTH: 11
<212> TYPE: PRT
<213> ORGANISM: Artificial sequence
<220> FEATURE:
<223> OTHER INFORMATION: IL-23p19 fragment

<400> SEQUENCE: 87

Gly Glu Pro Ser Leu Leu Pro Asp Ser Pro Val
1               5                   10

<210> SEQ ID NO 88
<211> LENGTH: 11
<212> TYPE: PRT
<213> ORGANISM: Artificial sequence
<220> FEATURE:
<223> OTHER INFORMATION: IL-23p19 fragment

<400> SEQUENCE: 88

Glu Pro Ser Leu Leu Pro Asp Ser Pro Val Gly
1               5                   10

<210> SEQ ID NO 89
<211> LENGTH: 11
<212> TYPE: PRT
<213> ORGANISM: Artificial sequence
<220> FEATURE:
<223> OTHER INFORMATION: IL-23p19 fragment

<400> SEQUENCE: 89

Pro Ser Leu Leu Pro Asp Ser Pro Val Gly Gln
1               5                   10

<210> SEQ ID NO 90
<211> LENGTH: 11
<212> TYPE: PRT
<213> ORGANISM: Artificial sequence
<220> FEATURE:
<223> OTHER INFORMATION: IL-23p19 fragment

<400> SEQUENCE: 90

Ser Leu Leu Pro Asp Ser Pro Val Gly Gln Leu
1               5                   10

-continued

```
<210> SEQ ID NO 91
<211> LENGTH: 12
<212> TYPE: PRT
<213> ORGANISM: Artificial sequence
<220> FEATURE:
<223> OTHER INFORMATION: IL-23p19 fragment

<400> SEQUENCE: 91

Gly Ser Asp Ile Phe Thr Gly Glu Pro Ser Leu Leu
1               5                   10

<210> SEQ ID NO 92
<211> LENGTH: 12
<212> TYPE: PRT
<213> ORGANISM: Artificial sequence
<220> FEATURE:
<223> OTHER INFORMATION: IL-23p19 fragment

<400> SEQUENCE: 92

Ser Asp Ile Phe Thr Gly Glu Pro Ser Leu Leu Pro
1               5                   10

<210> SEQ ID NO 93
<211> LENGTH: 12
<212> TYPE: PRT
<213> ORGANISM: Artificial sequence
<220> FEATURE:
<223> OTHER INFORMATION: IL-23p19 fragment

<400> SEQUENCE: 93

Asp Ile Phe Thr Gly Glu Pro Ser Leu Leu Pro Asp
1               5                   10

<210> SEQ ID NO 94
<211> LENGTH: 12
<212> TYPE: PRT
<213> ORGANISM: Artificial sequence
<220> FEATURE:
<223> OTHER INFORMATION: IL-23p19 fragment

<400> SEQUENCE: 94

Ile Phe Thr Gly Glu Pro Ser Leu Leu Pro Asp Ser
1               5                   10

<210> SEQ ID NO 95
<211> LENGTH: 12
<212> TYPE: PRT
<213> ORGANISM: Artificial sequence
<220> FEATURE:
<223> OTHER INFORMATION: IL-23p19 fragment

<400> SEQUENCE: 95

Phe Thr Gly Glu Pro Ser Leu Leu Pro Asp Ser Pro
1               5                   10

<210> SEQ ID NO 96
<211> LENGTH: 12
<212> TYPE: PRT
<213> ORGANISM: Artificial sequence
<220> FEATURE:
<223> OTHER INFORMATION: IL-23p19 fragment

<400> SEQUENCE: 96

Thr Gly Glu Pro Ser Leu Leu Pro Asp Ser Pro Val
1               5                   10

<210> SEQ ID NO 97
```

```
<211> LENGTH: 12
<212> TYPE: PRT
<213> ORGANISM: Artificial sequence
<220> FEATURE:
<223> OTHER INFORMATION: IL-23p19 fragment

<400> SEQUENCE: 97

Gly Glu Pro Ser Leu Leu Pro Asp Ser Pro Val Gly
1               5                   10

<210> SEQ ID NO 98
<211> LENGTH: 12
<212> TYPE: PRT
<213> ORGANISM: Artificial sequence
<220> FEATURE:
<223> OTHER INFORMATION: IL-23p19 fragment

<400> SEQUENCE: 98

Glu Pro Ser Leu Leu Pro Asp Ser Pro Val Gly Gln
1               5                   10

<210> SEQ ID NO 99
<211> LENGTH: 12
<212> TYPE: PRT
<213> ORGANISM: Artificial sequence
<220> FEATURE:
<223> OTHER INFORMATION: IL-23p19 fragment

<400> SEQUENCE: 99

Pro Ser Leu Leu Pro Asp Ser Pro Val Gly Gln Leu
1               5                   10

<210> SEQ ID NO 100
<211> LENGTH: 13
<212> TYPE: PRT
<213> ORGANISM: Artificial sequence
<220> FEATURE:
<223> OTHER INFORMATION: IL-23p19 fragment

<400> SEQUENCE: 100

Gly Ser Asp Ile Phe Thr Gly Glu Pro Ser Leu Leu Pro
1               5                   10

<210> SEQ ID NO 101
<211> LENGTH: 13
<212> TYPE: PRT
<213> ORGANISM: Artificial sequence
<220> FEATURE:
<223> OTHER INFORMATION: IL-23p19 fragment

<400> SEQUENCE: 101

Ser Asp Ile Phe Thr Gly Glu Pro Ser Leu Leu Pro Asp
1               5                   10

<210> SEQ ID NO 102
<211> LENGTH: 13
<212> TYPE: PRT
<213> ORGANISM: Artificial sequence
<220> FEATURE:
<223> OTHER INFORMATION: IL-23p19 fragment

<400> SEQUENCE: 102

Asp Ile Phe Thr Gly Glu Pro Ser Leu Leu Pro Asp Ser
1               5                   10

<210> SEQ ID NO 103
<211> LENGTH: 13
```

```
<212> TYPE: PRT
<213> ORGANISM: Artificial sequence
<220> FEATURE:
<223> OTHER INFORMATION: IL-23p19 fragment

<400> SEQUENCE: 103

Ile Phe Thr Gly Glu Pro Ser Leu Leu Pro Asp Ser Pro
1               5                   10

<210> SEQ ID NO 104
<211> LENGTH: 13
<212> TYPE: PRT
<213> ORGANISM: Artificial sequence
<220> FEATURE:
<223> OTHER INFORMATION: IL-23p19 fragment

<400> SEQUENCE: 104

Phe Thr Gly Glu Pro Ser Leu Leu Pro Asp Ser Pro Val
1               5                   10

<210> SEQ ID NO 105
<211> LENGTH: 13
<212> TYPE: PRT
<213> ORGANISM: Artificial sequence
<220> FEATURE:
<223> OTHER INFORMATION: IL-23p19 fragment

<400> SEQUENCE: 105

Thr Gly Glu Pro Ser Leu Leu Pro Asp Ser Pro Val Gly
1               5                   10

<210> SEQ ID NO 106
<211> LENGTH: 13
<212> TYPE: PRT
<213> ORGANISM: Artificial sequence
<220> FEATURE:
<223> OTHER INFORMATION: IL-23p19 fragment

<400> SEQUENCE: 106

Gly Glu Pro Ser Leu Leu Pro Asp Ser Pro Val Gly Gln
1               5                   10

<210> SEQ ID NO 107
<211> LENGTH: 13
<212> TYPE: PRT
<213> ORGANISM: Artificial sequence
<220> FEATURE:
<223> OTHER INFORMATION: IL-23p19 fragment

<400> SEQUENCE: 107

Glu Pro Ser Leu Leu Pro Asp Ser Pro Val Gly Gln Leu
1               5                   10

<210> SEQ ID NO 108
<211> LENGTH: 14
<212> TYPE: PRT
<213> ORGANISM: Artificial sequence
<220> FEATURE:
<223> OTHER INFORMATION: IL-23p19

<400> SEQUENCE: 108

Gly Ser Asp Ile Phe Thr Gly Glu Pro Ser Leu Leu Pro Asp
1               5                   10

<210> SEQ ID NO 109
<211> LENGTH: 14
<212> TYPE: PRT
```

```
<213> ORGANISM: Artificial sequence
<220> FEATURE:
<223> OTHER INFORMATION: IL-23p19 fragment

<400> SEQUENCE: 109

Ser Asp Ile Phe Thr Gly Glu Pro Ser Leu Leu Pro Asp Ser
1               5                   10

<210> SEQ ID NO 110
<211> LENGTH: 14
<212> TYPE: PRT
<213> ORGANISM: Artificial sequence
<220> FEATURE:
<223> OTHER INFORMATION: IL-23p19 fragment

<400> SEQUENCE: 110

Asp Ile Phe Thr Gly Glu Pro Ser Leu Leu Pro Asp Ser Pro
1               5                   10

<210> SEQ ID NO 111
<211> LENGTH: 14
<212> TYPE: PRT
<213> ORGANISM: Artificial sequence
<220> FEATURE:
<223> OTHER INFORMATION: IL-23p19 fragment

<400> SEQUENCE: 111

Ile Phe Thr Gly Glu Pro Ser Leu Leu Pro Asp Ser Pro Val
1               5                   10

<210> SEQ ID NO 112
<211> LENGTH: 14
<212> TYPE: PRT
<213> ORGANISM: Artificial sequence
<220> FEATURE:
<223> OTHER INFORMATION: IL-23p19 fragment

<400> SEQUENCE: 112

Phe Thr Gly Glu Pro Ser Leu Leu Pro Asp Ser Pro Val Gly
1               5                   10

<210> SEQ ID NO 113
<211> LENGTH: 14
<212> TYPE: PRT
<213> ORGANISM: Artificial sequence
<220> FEATURE:
<223> OTHER INFORMATION: IL-23p19 fragment

<400> SEQUENCE: 113

Thr Gly Glu Pro Ser Leu Leu Pro Asp Ser Pro Val Gly Gln
1               5                   10

<210> SEQ ID NO 114
<211> LENGTH: 14
<212> TYPE: PRT
<213> ORGANISM: Artificial sequence
<220> FEATURE:
<223> OTHER INFORMATION: IL-23p19 fragment

<400> SEQUENCE: 114

Gly Glu Pro Ser Leu Leu Pro Asp Ser Pro Val Gly Gln Leu
1               5                   10

<210> SEQ ID NO 115
<211> LENGTH: 15
<212> TYPE: PRT
<213> ORGANISM: Artificial sequence
```

```
<220> FEATURE:
<223> OTHER INFORMATION: IL-23p19 fragment

<400> SEQUENCE: 115

Gly Ser Asp Ile Phe Thr Gly Glu Pro Ser Leu Leu Pro Asp Ser
1               5                   10                  15

<210> SEQ ID NO 116
<211> LENGTH: 15
<212> TYPE: PRT
<213> ORGANISM: Artificial sequence
<220> FEATURE:
<223> OTHER INFORMATION: IL-23p19 fragment

<400> SEQUENCE: 116

Ser Asp Ile Phe Thr Gly Glu Pro Ser Leu Leu Pro Asp Ser Pro
1               5                   10                  15

<210> SEQ ID NO 117
<211> LENGTH: 15
<212> TYPE: PRT
<213> ORGANISM: Artificial sequence
<220> FEATURE:
<223> OTHER INFORMATION: IL-23p19 fragment

<400> SEQUENCE: 117

Asp Ile Phe Thr Gly Glu Pro Ser Leu Leu Pro Asp Ser Pro Val
1               5                   10                  15

<210> SEQ ID NO 118
<211> LENGTH: 15
<212> TYPE: PRT
<213> ORGANISM: Artificial sequence
<220> FEATURE:
<223> OTHER INFORMATION: IL-23p19 fragment

<400> SEQUENCE: 118

Ile Phe Thr Gly Glu Pro Ser Leu Leu Pro Asp Ser Pro Val Gly
1               5                   10                  15

<210> SEQ ID NO 119
<211> LENGTH: 15
<212> TYPE: PRT
<213> ORGANISM: Artificial sequence
<220> FEATURE:
<223> OTHER INFORMATION: IL-23p19 fragment

<400> SEQUENCE: 119

Phe Thr Gly Glu Pro Ser Leu Leu Pro Asp Ser Pro Val Gly Gln
1               5                   10                  15

<210> SEQ ID NO 120
<211> LENGTH: 15
<212> TYPE: PRT
<213> ORGANISM: Artificial sequence
<220> FEATURE:
<223> OTHER INFORMATION: IL-23p19

<400> SEQUENCE: 120

Thr Gly Glu Pro Ser Leu Leu Pro Asp Ser Pro Val Gly Gln Leu
1               5                   10                  15

<210> SEQ ID NO 121
<211> LENGTH: 16
<212> TYPE: PRT
<213> ORGANISM: Artificial sequence
<220> FEATURE:
```

```
<223> OTHER INFORMATION: IL-23p19 fragment

<400> SEQUENCE: 121

Gly Ser Asp Ile Phe Thr Gly Glu Pro Ser Leu Leu Pro Asp Ser Pro
1               5                   10                  15

<210> SEQ ID NO 122
<211> LENGTH: 16
<212> TYPE: PRT
<213> ORGANISM: Artificial sequence
<220> FEATURE:
<223> OTHER INFORMATION: IL-23p19 fragment

<400> SEQUENCE: 122

Ser Asp Ile Phe Thr Gly Glu Pro Ser Leu Leu Pro Asp Ser Pro Val
1               5                   10                  15

<210> SEQ ID NO 123
<211> LENGTH: 16
<212> TYPE: PRT
<213> ORGANISM: Artificial sequence
<220> FEATURE:
<223> OTHER INFORMATION: IL-23p19 fragment

<400> SEQUENCE: 123

Asp Ile Phe Thr Gly Glu Pro Ser Leu Leu Pro Asp Ser Pro Val Gly
1               5                   10                  15

<210> SEQ ID NO 124
<211> LENGTH: 16
<212> TYPE: PRT
<213> ORGANISM: Artificial sequence
<220> FEATURE:
<223> OTHER INFORMATION: IL-23p19 fragment

<400> SEQUENCE: 124

Ile Phe Thr Gly Glu Pro Ser Leu Leu Pro Asp Ser Pro Val Gly Gln
1               5                   10                  15

<210> SEQ ID NO 125
<211> LENGTH: 16
<212> TYPE: PRT
<213> ORGANISM: Artificial sequence
<220> FEATURE:
<223> OTHER INFORMATION: IL-23p19 fragment

<400> SEQUENCE: 125

Phe Thr Gly Glu Pro Ser Leu Leu Pro Asp Ser Pro Val Gly Gln Leu
1               5                   10                  15

<210> SEQ ID NO 126
<211> LENGTH: 17
<212> TYPE: PRT
<213> ORGANISM: Artificial sequence
<220> FEATURE:
<223> OTHER INFORMATION: IL-23p19 fragment

<400> SEQUENCE: 126

Gly Ser Asp Ile Phe Thr Gly Glu Pro Ser Leu Leu Pro Asp Ser Pro
1               5                   10                  15

Val

<210> SEQ ID NO 127
<211> LENGTH: 17
<212> TYPE: PRT
<213> ORGANISM: Artificial sequence
```

```
<220> FEATURE:
<223> OTHER INFORMATION: IL-23p19 fragment

<400> SEQUENCE: 127

Ser Asp Ile Phe Thr Gly Glu Pro Ser Leu Leu Pro Asp Ser Pro Val
1               5                   10                  15

Gly

<210> SEQ ID NO 128
<211> LENGTH: 17
<212> TYPE: PRT
<213> ORGANISM: Artificial sequence
<220> FEATURE:
<223> OTHER INFORMATION: IL-23p19 fragment

<400> SEQUENCE: 128

Asp Ile Phe Thr Gly Glu Pro Ser Leu Leu Pro Asp Ser Pro Val Gly
1               5                   10                  15

Gln

<210> SEQ ID NO 129
<211> LENGTH: 17
<212> TYPE: PRT
<213> ORGANISM: Artificial sequence
<220> FEATURE:
<223> OTHER INFORMATION: IL-23p19 fragment

<400> SEQUENCE: 129

Ile Phe Thr Gly Glu Pro Ser Leu Leu Pro Asp Ser Pro Val Gly Gln
1               5                   10                  15

Leu

<210> SEQ ID NO 130
<211> LENGTH: 18
<212> TYPE: PRT
<213> ORGANISM: Artificial sequence
<220> FEATURE:
<223> OTHER INFORMATION: IL-23p19 fragment

<400> SEQUENCE: 130

Gly Ser Asp Ile Phe Thr Gly Glu Pro Ser Leu Leu Pro Asp Ser Pro
1               5                   10                  15

Val Gly

<210> SEQ ID NO 131
<211> LENGTH: 18
<212> TYPE: PRT
<213> ORGANISM: Artificial sequence
<220> FEATURE:
<223> OTHER INFORMATION: IL-23p19 fragment

<400> SEQUENCE: 131

Ser Asp Ile Phe Thr Gly Glu Pro Ser Leu Leu Pro Asp Ser Pro Val
1               5                   10                  15

Gly Gln

<210> SEQ ID NO 132
<211> LENGTH: 18
<212> TYPE: PRT
<213> ORGANISM: Artificial sequence
<220> FEATURE:
<223> OTHER INFORMATION: IL-23p19 fragment

<400> SEQUENCE: 132
```

Asp Ile Phe Thr Gly Glu Pro Ser Leu Leu Pro Asp Ser Pro Val Gly
1               5                   10                  15

Gln Leu

<210> SEQ ID NO 133
<211> LENGTH: 19
<212> TYPE: PRT
<213> ORGANISM: Artificial sequence
<220> FEATURE:
<223> OTHER INFORMATION: IL-23p19 fragment

<400> SEQUENCE: 133

Gly Ser Asp Ile Phe Thr Gly Glu Pro Ser Leu Leu Pro Asp Ser Pro
1               5                   10                  15

Val Gly Gln

<210> SEQ ID NO 134
<211> LENGTH: 19
<212> TYPE: PRT
<213> ORGANISM: Artificial sequence
<220> FEATURE:
<223> OTHER INFORMATION: IL-23p19 fragment

<400> SEQUENCE: 134

Ser Asp Ile Phe Thr Gly Glu Pro Ser Leu Leu Pro Asp Ser Pro Val
1               5                   10                  15

Gly Gln Leu

<210> SEQ ID NO 135
<211> LENGTH: 20
<212> TYPE: PRT
<213> ORGANISM: Artificial sequence
<220> FEATURE:
<223> OTHER INFORMATION: IL-23p19 fragment

<400> SEQUENCE: 135

Ala Ser Asp Ile Phe Thr Gly Glu Pro Ser Leu Leu Pro Asp Ser Pro
1               5                   10                  15

Val Ala Gln Leu
            20

<210> SEQ ID NO 136
<211> LENGTH: 20
<212> TYPE: PRT
<213> ORGANISM: Artificial sequence
<220> FEATURE:
<223> OTHER INFORMATION: IL-23p19 fragment

<400> SEQUENCE: 136

Ala Ser Asp Ile Phe Thr Gly Glu Pro Ser Leu Leu Pro Asp Ser Pro
1               5                   10                  15

Val Gly Gln Leu
            20

<210> SEQ ID NO 137
<211> LENGTH: 20
<212> TYPE: PRT
<213> ORGANISM: Artificial sequence
<220> FEATURE:
<223> OTHER INFORMATION: IL-23p19 fragment

<400> SEQUENCE: 137

Gly Ser Asp Ile Phe Thr Gly Glu Pro Ser Leu Leu Pro Asp Ser Pro

```
1               5                   10                  15

Val Ala Gln Leu
            20

<210> SEQ ID NO 138
<211> LENGTH: 20
<212> TYPE: PRT
<213> ORGANISM: Artificial sequence
<220> FEATURE:
<223> OTHER INFORMATION: IL-23p19 fragment

<400> SEQUENCE: 138

Asp Ser Asp Ile Phe Thr Gly Glu Pro Ala Leu Leu Pro Asp Ser Pro
1               5                   10                  15

Val Glu Gln Leu
            20

<210> SEQ ID NO 139
<211> LENGTH: 21
<212> TYPE: PRT
<213> ORGANISM: Artificial sequence
<220> FEATURE:
<223> OTHER INFORMATION: IL-23p19 fragment

<400> SEQUENCE: 139

Tyr Glu Lys Leu Leu Gly Ser Asp Ile Cys Thr Gly Glu Pro Ser Leu
1               5                   10                  15

Leu Pro Asp Ser Pro
            20

<210> SEQ ID NO 140
<211> LENGTH: 25
<212> TYPE: PRT
<213> ORGANISM: Artificial sequence
<220> FEATURE:
<223> OTHER INFORMATION: IL-23p19 fragment

<400> SEQUENCE: 140

Tyr Glu Lys Leu Cys Gly Ser Asp Ile Phe Thr Gly Glu Pro Ser Leu
1               5                   10                  15

Leu Pro Asp Ser Pro Val Gly Gln Leu
            20                  25

<210> SEQ ID NO 141
<211> LENGTH: 26
<212> TYPE: PRT
<213> ORGANISM: Artificial sequence
<220> FEATURE:
<223> OTHER INFORMATION: IL-23p19 fragment

<400> SEQUENCE: 141

Lys Leu Leu Gly Ser Asp Ile Phe Thr Gly Glu Pro Ser Leu Leu Pro
1               5                   10                  15

Asp Ser Pro Val Gly Gln Leu His Ala Ser
            20                  25
```

METHOD OF VACCINATION FOR LIMITING ARTICULAR INFLAMMATION IN RHEUMATOID ARTHRITIS AND MULTIPLE SCLEROSIS BY ADMINISTERING IL-23 PEPTIDES

The present application claims the benefit of U.S. provisional application Ser. No. 61/244,324 filed on Sep. 21, 2009, which is incorporated herein by reference.

FIELD OF THE INVENTION

The present invention deals with the field of bone resorption diseases and immune-related diseases, such as inflammatory diseases, in particular rheumatoid arthritis, multiple sclerosis, inflammatory bowel diseases, and cancers, and more precisely to new polypeptides and uses thereof in immune-related diseases therapy.

BACKGROUND OF THE INVENTION

1—The Role of IL-23 in the Immune System

IL-23 is a recently discovered cytokine, secreted mainly by activated dendritic cells, monocytes and macrophages. It comprises two subunits linked by a disulfide bond, designated by p19 and p40 (Oppmann B et al., *Immunity*, 13(5), pp 715-25, 2000). The human p40 subunit contains 328 amino-acids and is shared between the cytokine IL-12 and IL-23. The human p19 subunit, which contains 189 amino-acids, is specific of IL-23 and participates in the binding of IL-23 with its receptor (Parham C et al., *J Immunol*, 168(11), pp 5699-708, 2002). IL-23 is known to promote a specific T cell activation state characterized by the production of IL-17, a cytokine frequently over-expressed in several inflammatory diseases (Aggarwal S et al., 278(3), pp 1910-4, 2003). IL-23 acts preferentially on memory T cells rather than on naïve T cells, supporting its role in long term inflammation and in particular in the survival and expansion of autoreactive cells in autoimmune disorders.

Initial findings showed that the transgenic expression of IL-23 in an animal model induces a severe systemic inflammation marked notably in many key organs such as the skin or the digestive tract (Wiekowski M T et al., *J Immunol*, 166(12), pp 7563-70, 2001). These findings prompted the investigators to study a possible role for IL-23 in diseases like psoriasis or inflammatory bowel disease. Today it is well known that IL-23 drives the inflammatory events leading to severe intestinal inflammation in mice (Kullberg M C et al., *J Exp Med*, 203(11), pp 2485-94, 2006; Hue S et al., *J Exp Med*, 203(11), pp 2473-83, 2006) and that functional IL-23R variants are strongly linked to inflammatory bowel disease in human (Duerr R H et al., *Science*, 314(5804), pp 1461-3, 2006). Similarly, a disease-promoting role for IL-23 has been described in autoimmune inflammation in the brain (Cua D J et al., *Nature*, 421(6924), pp 744-8, 2003), in joints during autoimmune arthritis (Murphy C A et al., *J Exp Med*, 198(12), pp 1951-7, 2003), in the skin during psoriasis (Lee E et al., *J Exp Med*, 199(1), pp 125-30, 2004) and even in the incidence and growth of certain tumours (Langowski J L et al., *Nature*, 442(7101), pp 461-5, 2006). In addition, IL-23 is also known to play a role in the development of various diseases characterized by an excessive bone resorption, with or without inflammation, such as in osteoporosis (Kim et al. (2008) *Exp Mol Med*. 40:418-26). In contrast with the blockade of IL-12, the specific antagonism of IL-23 through its p19 subunit has indeed the potential of strongly improving many organ-specific diseases without compromising long-term protective responses in the patients.

2—Existing Antagonists of IL-23

In order to specifically block the activity of a desired cytokine, macromolecules and particularly antibodies or soluble receptors to this cytokine have been used. The therapeutic use of antibodies against the common subunit p40 of the human IL-12 and human IL-23 has been disclosed in International patent application WO 04/101750. Similarly, the use of inhibitory macromolecules binding to the subunit p19 of human IL-23 has been disclosed in patent applications WO 07/005,955, WO 08/103,473, and U.S. Ser. No. 09/012,3479. The use of monoclonal antibodies directed simultaneously against the subunits p19 and p40 or against the IL-23-specific receptor has also been disclosed in International patent application WO 04/042009. Finally, the use of antibodies against one or both human IL-23 and its downstream effector cytokine IL-17 has been disclosed in International patent application WO 07/027,761. An alternative approach to the passive infusion of inhibitors is to use an active immunization against cytokines as disclosed in International patent application WO 03/084979.

3—The Current Art in Active Immunization Against IL-23

A method of vaccination to fight autoimmune diseases, comprising the subunit p35 of IL-12 or the common subunit p40 for IL-12 and IL-23, has been disclosed in International patent application WO 05/058349. A method of vaccination against some IL-23 peptides has been previously disclosed by our group in International application WO 03/084979, in particular against the peptide LLP DSP VGQ LHA SLL GLS Q (SEQ ID NO: 1). Peptides derived from IL-23p19 are also disclosed in International application WO 2005/108425.

SUMMARY OF THE INVENTION

In a first aspect, the present invention relates to a compound comprising, or consisting of, a polypeptide, in particular a cyclised polypeptide, wherein the compound does not comprise IL-23p19, in particular human IL-23p19. In an aspect, the polypeptide may comprise an amino acid sequence selected in the group consisting of GSD IFT GEP SLL PDS PVG QL (SEQ ID NO: 2), fragments of at least 5 amino acids, derivatives of fragments of at least 6 amino acids, and derivatives, with the exclusion of the IL-23 polypeptides described in the International patent application WO 03/084979. In another aspect, the polypeptide comprises, or consists of, at least 11 contiguous amino acids selected from:

a first sequence $X_1$-S-D-I-F-$X_2$-G-E-P-$X_3$-L-$X_4$-P-$X_5$-$X_6$-$X_7$-$X_8$-$X_9$-Q-L (SEQ ID NO: 13), wherein:

$X_1$ represents G, D; or A
$X_2$ represents T or K;
$X_3$ represents S, P, or A;
$X_4$ represents L, H, or F;
$X_5$ represents D or N;
$X_6$ represents G, S, or D;
$X_7$ represents P or S;
$X_8$ represents V or M;
$X_9$ represents G, D, S, E, or A; or
a second sequence presenting at least 90% identity with the first sequence provided that a peptide consisting of the second sequence is liable to elicit antibodies directed against IL-23.

In a second aspect, the present invention relates to a polypeptide as defined above.

In a third aspect, the present invention relates to a nucleic acid encoding a polypeptide as described above, wherein said nucleic acid may be delivered in vivo alone or in association with a vector.

In a fourth aspect, the present invention relates to an antibody directed against the polypeptide of the invention, which antibody recognizes the region of human IL-23p19 from Gly[105] to Leu[124] (SEQ ID NO: 24) or the region of mouse IL-23p19 from Asp$^{106}$ to Leu$^{125}$ (SEQ ID NO: 3). The present invention also relates to an antibody, a scFV, or an aptamer, which is specific for a polypeptide as defined above, and to pharmaceutical compositions comprising them.

In a fifth aspect, the present invention relates to a pharmaceutical composition comprising a pharmaceutically acceptable vehicle in association with, in particular as an active substance, at least one compound as defined above, a polypeptide as described above, a nucleic acid encoding thereof, or a nucleic acid vector comprising said nucleic acid.

In a sixth aspect, the present invention relates to the use of at least one compound as defined above, a polypeptide as described above, a nucleic acid sequence coding therefore, a vector comprising such a nucleic acid sequence, or a pharmaceutical composition as described previously for preventing or treating an immune-related disease or a bone resorption disease in a subject, or for the manufacture of a medicament intended for treating an immune-related disease or a bone resorption disease in a subject. The present invention also relates to a compound as defined above, a pharmaceutical composition as defined above, a polypeptide as described above, a nucleic acid sequence coding therefore, a vector comprising such a nucleic acid sequence, for use in the prevention or treatment of an immune-related disease or a bone resorption disease in a subject.

In a seventh aspect, the present invention relates to a method for preventing or treating an immune-related disease or a bone-resorption disease in a subject, comprising administering to the subject a therapeutically effective amount of at least one compound as defined above, a polypeptide as described above, a nucleic acid sequence coding therefore, a vector comprising such a nucleic acid sequence, or a pharmaceutical composition as described previously.

In a eighth aspect, the present invention relates to the in vitro use of a compound as defined above for preparing specific ligands of IL-23, in particular anti-IL-23 scFvs or anti-IL-23 aptamers. The present invention also relates to a method, in particular an in vitro method, for obtaining anti-IL-23 antibodies or anti-IL-23 antibody-producing cells, comprising a step of recovering anti-IL-23 antibodies or anti-IL-23 antibody-producing cells from a biological sample obtained from an animal which has been administered with a pharmaceutical composition as defined above or a compound as defined above. The present invention further relates to the anti-IL23 antibodies, scFVs and aptamers liable to be obtained by the above method and use, as well as to pharmaceutical compositions comprising them.

DETAILED DESCRIPTION OF THE INVENTION

Figure 1:
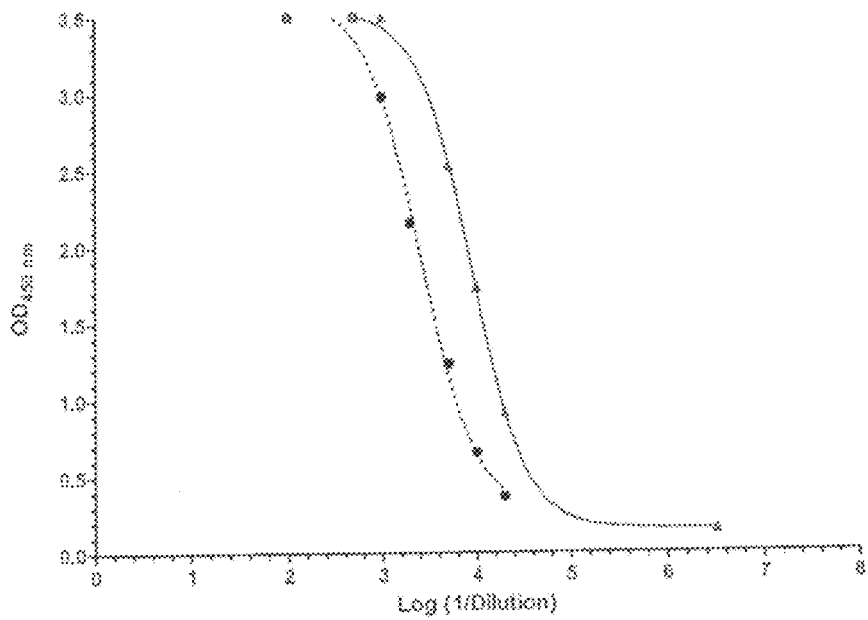
FIG. 1 shows that the epitopes of the human IL-23 peptide lead to antibodies cross-reacting with human IL-23 and with murine IL-23.

The inventors have now discovered new peptides derived from a region of the p19 subunit of IL-23 cytokine (IL-23p19) which can be used to elicit therapeutic antibodies either by active immunization in the patient himself or by passive infusion of oligoclonal/monoclonal antibodies that can be reinfused in the patient after large-scale production.

In fact, the inventors have demonstrated that immunization of rabbits against a peptide derivative of human IL-23 subunit p19 from the specific region Gly$^{105}$ to Leu$^{124}$: GSD IFT GEP SLL PDS PVG QL (SEQ ID NO: 2) could generate antibodies recognizing the whole human IL-23 cytokine (Example 1) and moreover that these antibodies could neutralize the biological activity of the human cytokine (Example 2). The immunizing peptide was a cyclised version of the region Gly$^{105}$ to Leu$^{124}$, with two supplementary terminal cysteines for cyclisation, and a supplementary tyrosine on the C-terminal of the peptide for the coupling with bis-diazo-benzidine (BDB). The inventors have also demonstrated a cross-species reactivity: the same antibodies could recognize the murine IL-23 cytokine (Example 1) and neutralize its biological activity (Example 3).

The reciprocal results were also demonstrated: after immunizing rabbits against the murine equivalent of the previously described peptide derivative of mouse IL-23p19: DSD IFK GEP ALL PDS PME QL (SEQ ID NO: 3). The immunizing peptide was a cyclised version of the described sequence, with two supplementary cysteines for cyclisation, and was coupled to KLH via glutaraldehyde. The generated antibodies could recognize both the murine and human IL-23 cytokines (by ELISA) and they could also neutralize the biological activity of both cytokines (Example 4).

Finally, the inventors have show that anti-mIL-23 Abs could be generated in mice following immunization with the previously described peptide derivative of mouse IL-23p19 DSD IFK GEP ALL PDS PME QL (SEQ ID NO: 3), showing that it is possible to overcome the immune tolerance against self (Example 5).

The inventors have shown that the cyclised peptide derivative of mouse IL-23p19, KGE PAL LPD SP (SEQ ID NO: 4), could generate antibodies recognizing both the murine and the human IL-23 and that these antibodies also had a neutralizing activity against both cytokines (Example 6). Similar results were obtained with the corresponding human subsequence TGE PSL LPD SP (SEQ ID NO: 5) (Example 7).

The inventors have demonstrated that two human subsequences of size 5 derived from the above peptide can also generate antibodies recognizing the native cytokine C-TGE PS-C (SEQ ID NO: 6) and C-LPD SP-C-Y (SEQ ID NO: 7) and exhibit a neutralizing activity of human IL-23 (Example 8). It shows that an epitope size may be as small as 5 amino-acids.

Finally, IL-23 has been involved in the pathogenesis of many autoimmune diseases and the inventors tested the ability of the cyclised peptide DSD IFK GEP ALL PDS PME QL (SEQ ID NO: 3) of murine IL-23 to exhibit a protection against a typical model of autoimmune disease in mice. For that the inventors used the collagen-induced arthritis mouse model, a model for rheumatoid arthritis. The peptide exhibited a significant protective effect against disease when comparing groups of mice immunized against the peptide with groups of mice immunized against KLH alone or mice immunized with the vehicle (PBS) (Example 9).

Moreover, the inventors have also established a preliminary proof of efficacy of the immunization with the same peptide of IL-23 in a treatment against experimental autoimmune encephalomyelitis, a well-known model of multiple sclerosis (Example 10).

Overall, the described specific peptide region of IL-23 appears to be a good target to generate neutralizing antibodies against the native cytokine. The inventors have shown that modifications in the sequence of the peptide, including cross-species similarities in amino acids, could still lead to the generation of active antibodies.

As will be clear to one of skill in the art, where the compound of the invention "comprises" a polypeptide according to the invention, other molecules may be present in addition to the polypeptide.

In any case, the compound of the invention is such that it does not comprise IL-23p19, in particular IL-23p19 from *Homo sapiens, Macaca mulatta, Pan troglodytes, Felis catus, Canis lupus familiaris, Carollia perspicillata, Rattus norvegicus, Peromyscus maniculatus, Onychomys leucogaster, Cervus elaphus, Equus caballus, Bos taurus, Sus scrofa, Cavia porcellus,* or *Mus musculus*.

In addition, according to a preferred embodiment of the invention, the compound of the invention does not comprise fragments of IL23p19, in particular from *Homo sapiens, Macaca mulatta, Pan troglodytes, Felis catus, Canis lupus familiaris, Carollia perspicillata, Rattus norvegicus, Peromyscus maniculatus, Onychomys leucogaster, Cervus elaphus, Equus caballus, Bos taurus, Sus scrofa, Cavia porcellus,* or *Mus musculus*, of at least 22 amino acids which include the polypeptide of the invention. Thus, according to this embodiment and by way of example, the polypeptide of the invention may comprise the 11 N-terminal contiguous amino acids of SEQ ID NO: 13, along with a stretch of one or more amino acids from IL-23p19 on the N-terminal side of the 11 contiguous amino acids, thereby reconstituting a fragment of IL-23p19, as long as the fragment of IL-23p19 comprises 21 amino acids or less.

Besides, in a particular aspect, the invention relates to a new polypeptide comprising an amino acid sequence selected in the group consisting of GSD IFT GEP SLL PDS PVG QL (SEQ ID NO: 2), fragments of at least 5 amino acids, derivatives of fragments of at least 6 amino acids, and derivatives, with the exclusion of the IL-23 polypeptides described in the International patent application WO 03/084979.

A consequence of the observation disclosed above is also that peptides as small as 5 amino-acids derived from the peptide GSD IFT GEP SLL PDS PVG QL (SEQ ID No 2) can also generate antibodies recognizing IL-23 cytokine. Peptide stretches of 5 amino-acids or more derived from the sequence can thus be effective to generate antibodies recognizing the native cytokine.

The polypeptide of the invention is able to induce the production of antibodies recognizing the region of human IL-23p19 from $Gly^{105}$ to $Leu^{124}$ or the region of mouse IL-23p19 from $Asp^{106}$ to $Leu^{125}$ as detected by ELISA.

As used herein the term "fragments" refers to polypeptides having a length of at least 5 amino acids, as an example a length of at least 6 amino acids, preferably at least 8 amino acids, as an example of at least of 10 amino acids and more preferably at least 12 amino acids, as an example of at least 13 amino acids with the exclusion of the IL-23 polypeptides described in the International patent application WO 03/084979.

In particular according to the present invention, fragment of 5 amino acids from an amino sequence have a percentage of identity of 100% with said amino acid sequence.

As used herein the term "derivatives" of amino acid sequence refers to polypeptides having a percentage of identity of at least 75%, preferably of 80%, possibly 85%, for example 90% with said amino acid sequence.

In particular, according to the present invention, when referring to derivatives of fragments from the amino sequence GSD IFT GEP SLL PDS PVG QL (SEQ ID NO: 2), the term "derivatives" refers to fragments of at least 6 amino acids from said amino acid sequence.

The term "derivatives" also refers to peptides having a percentage of identity of at least 75%, preferably of 80%, possibly 85%, for example 90% with said amino acid sequence, or possibly corresponding to a reverse sequence derived from said amino acid sequence, for instance VPS DPL LSP EGT FID (SEQ ID NO: 8).

According to the present invention, the preferred length of the polypeptide of the invention is equal or less than 50 amino acids, preferably equal or less than 40, possibly equal or less than 35, as an example equal or less than 32, or possibly again equal or less than 28 amino acids, and more preferably equal or less than 25 amino acids.

In a preferred embodiment of the present invention, the polypeptide of the invention comprises an amino acid sequence selected in the group comprising $X_2$-G-E-P-$X_3$-L-$X_4$-P-$X_5$-$X_6$-$X_7$ (SEQ ID NO: 9) of at least 5 amino acids with the exclusion of the IL-23 polypeptides described in the International application WO 03/084979, and derivatives of at least 80% of identity thereof;

wherein $X_2$ is T or K, preferably T;
$X_3$ is S, P or A, preferably S;
$X_4$ is L, F or H, preferably L;
$X_5$ is D or N, preferably D;
$X_6$ is S, G or D, preferably S or G, and more preferably S;
$X_7$ is P or S, preferably P.

Advantageously, said polypeptide comprises (i) an amino acid sequence selected in the group comprising TGE PSL LPD SP (SEQ ID NO: 5) from *Homo sapiens*, from *Macaca mulatta*, from *Pan troglodytes*, from *Felis catus*, and from *Rattus norvegicus*, TGE PSL LPD GP (SEQ ID NO: 10) from *Canis lupus* familiaris, from *Carollia perspicillata*, from *Onychomys leucogaster*, and from *Cervus elaphus*, TGE PSL LPD DP (SEQ ID NO: 11) from *Peromyscus maniculatus*, TGE PSL LPN GP (SEQ ID NO: 12) from *Equus caballus*, and from *Bos taurus*, and KGE PAL LPD SP (SEQ ID NO: 4) from *Mus musculus*, fragments and derivatives thereof.

In another preferred embodiment of the invention, the polypeptide of the invention comprises an amino acid sequence selected in the group comprising $X_1$-S-D-I-F-$X_2$-G-E-P-$X_3$-L-$X_4$-P-$X_5$-$X_6$-$X_7$-$X_8$-$X_9$-Q-L (SEQ ID NO: 13), fragments of at least 6 amino acids, preferably of at least 8 amino acids, with the exclusion of the IL-23 polypeptides described in the International patent application WO 03/084979, and derivatives of at least 75% of identity thereof;

wherein $X_1$ is G, or D, preferably G;
$X_2$ is T or K, preferably T;
$X_3$ is S, P or A, preferably S;
$X_4$ is L, F or H, preferably L;
$X_5$ is D or N, preferably D;
$X_6$ is S, G or D, preferably S;
$X_7$ is P or S, preferably P;
$X_8$ is V or M, preferably V;

$X_9$ is G, S, E, or D, preferably G, D or S, and more preferably G or D.

Alternatively, in another aspect of the invention, the polypeptide according to the invention preferably comprises, or consists of, at least 11 contiguous amino acids selected from:

a first sequence $X_1$-S-D-I-F-$X_2$-G-E-P-$X_3$-L-$X_4$-P-$X_5$-$X_6$-$X_7$-$X_8$-$X_9$-Q-L (SEQ ID NO: 13), wherein:
$X_1$ represents G, D, or A, preferably G;
$X_2$ represents T or K, preferably T;
$X_3$ represents S, P, or A, preferably S;
$X_4$ represents L, H, or F, preferably L;
$X_5$ represents D or N, preferably D;
$X_6$ represents G, S, or D, preferably S;
$X_7$ represents P or S, preferably P;
$X_8$ represents V or M, preferably V;
$X_9$ represents G, D, S, E, or A, preferably G, D or S, and more preferably G or D; or a second sequence presenting at least 90%, preferably 95%, more preferably 98%, identity with the first sequence provided that a peptide consisting of the second sequence is liable to elicit antibodies directed against IL-23.

As intended herein, the percentage of identity of a first peptide sequence vis-à-vis a second peptide sequence may be determined by performing an optimal full-length alignment of the two sequences, determining the number of aligned positions for which amino acids are identical in the two sequences and dividing this number by the total number of amino acids in the longest of the two sequences. As intended herein, an "optimal alignment" between two sequences is such that it yields the maximum percentage of identity between the two sequences.

As intended herein, a peptide is "liable to elicit antibodies directed against IL-23" in particular if antibodies obtained from an animal, such as a mouse, immunized by the peptide, may bind to IL-23. Methods for immunizing an animal with a peptide are well-known to one of skill in the art and may notably comprise the use of carrier proteins and/or adjuvants. In addition, as will be clear to one of skill in the art, the antibodies elicited by the peptide may bind to IL-23 in conditions preventing non-specific binding, i.e. in conditions wherein the antibodies do not bind to proteins unrelated to IL-23.

Preferably, the first above defined first sequence comprises, or consists of:

(SEQ ID NO: 25)
$X_1SDIFX_2GEPX_3L$;

(SEQ ID NO: 26)
$SDIFX_2GEPX_3LX_4$;

(SEQ ID NO 27)
$DIFX_2GEPX_3LX_4P$;

(SEQ ID NO: 28)
$IFX_2GEPX_3LX_4PX_5$;

(SEQ ID NO: 29)
$FX_2GEPX_3LX_4PX_5X_6$;

(SEQ ID NO: 30)
$X_2GEPX_3LX_4PX_5X_6X_7$;

(SEQ ID NO: 31)
$GEPX_3LX_4PX_5X_6X_7X_8$;

(SEQ ID NO: 32)
$EPX_3LX_4PX_5X_6X_7X_8X_9$;

-continued (SEQ ID NO: 33)
$PX_3LX_4PX_5X_6X_7X_8X_9Q$;

(SEQ ID NO: 34)
$X_3LX_4PX_5X_6X_7X_8X_9QL$;

(SEQ ID NO: 35)
$X_1SDIFX_2GEPX_3LX_4$;

(SEQ ID NO: 36)
$SDIFX_2GEPX_3LX_4P$;

(SEQ ID NO: 37)
$DIFX_2GEPX_3LX_4PX_5$;

(SEQ ID NO: 38)
$IFX_2GEPX_3LX_4PX_5X_6$;

(SEQ ID NO: 39)
$FX_2GEPX_3LX_4PX_5X_6X_7$;

(SEQ ID NO: 40)
$X_2GEPX_3LX_4PX_5X_6X_7X_8$;

(SEQ ID NO: 41)
$GEPX_3LX_4PX_5X_6X_7X_8X_9$;

(SEQ ID NO: 42)
$EPX_3LX_4PX_5X_6X_7X_8X_9Q$;

(SEQ ID NO: 43)
$PX_3LX_4PX_5X_6X_7X_8X_9QL$;

(SEQ ID NO: 44)
$X_1SDIFX_2GEPX_3LX_4P$;

(SEQ ID NO: 45)
$SDIFX_2GEPX_3LX_4PX_5$;

(SEQ ID NO: 46)
$DIFX_2GEPX_3LX_4PX_5X_6$;

(SEQ ID NO: 47)
$IFX_2GEPX_3LX_4PX_5X_6X_7$;

(SEQ ID NO: 48)
$FX_2GEPX_3LX_4PX_5X_6X_7X_8$;

(SEQ ID NO: 49)
$X_2GEPX_3LX_4PX_5X_6X_7X_8X_9$;

(SEQ ID NO: 50)
$GEPX_3LX_4PX_5X_6X_7X_8X_9Q$;

(SEQ ID NO: 51)
$EPX_3LX_4PX_5X_6X_7X_8X_9QL$;

(SEQ ID NO: 52)
$X_1SDIFX_2GEPX_3LX_4PX_5$;

(SEQ ID NO: 53)
$SDIFX_2GEPX_3LX_4PX_5X_6$;

(SEQ ID NO: 54)
$DIFX_2GEPX_3LX_4PX_5X_6X_7$;

(SEQ ID NO: 55)
$IFX_2GEPX_3LX_4PX_5X_6X_7X_8$;

(SEQ ID NO: 56)
$FX_2GEPX_3LX_4PX_5X_6X_7X_8X_9$;

(SEQ ID NO: 57)
$X_2GEPX_3LX_4PX_5X_6X_7X_8X_9Q$;

(SEQ ID NO: 58)
$GEPX_3LX_4PX_5X_6X_7X_8X_9QL$;

(SEQ ID NO: 59)
$X_1SDIFX_2GEPX_3LX_4PX_5X_6$;

SDIFX$_2$GEPX$_3$LX$_4$PX$_5$X$_6$X$_7$; (SEQ ID NO: 60)

DIFX$_2$GEPX$_3$LX$_4$PX$_5$X$_6$X$_7$X$_8$; (SEQ ID NO: 61)

IFX$_2$GEPX$_3$LX$_4$PX$_5$X$_6$X$_7$X$_8$X$_9$; (SEQ ID NO: 62)

FX$_2$GEPX$_3$LX$_4$PX$_5$X$_6$X$_7$X$_8$X$_9$Q; (SEQ ID NO: 63)

X$_2$GEPX$_3$LX$_4$PX$_5$X$_6$X$_7$X$_8$X$_9$QL; (SEQ ID NO: 64)

X$_1$SDIFX$_2$GEPX$_3$LX$_4$PX$_5$X$_6$X$_7$; (SEQ ID NO: 65)

SDIFX$_2$GEPX$_3$LX$_4$PX$_5$X$_6$X$_7$X$_8$; (SEQ ID NO: 66)

DIFX$_2$GEPX$_3$LX$_4$PX$_5$X$_6$X$_7$X$_8$X$_9$; (SEQ ID NO: 67)

IFX$_2$GEPX$_3$LX$_4$PX$_5$X$_6$X$_7$X$_8$X$_9$Q; (SEQ ID NO: 68)

FX$_2$GEPX$_3$LX$_4$PX$_5$X$_6$X$_7$X$_8$X$_9$QL; (SEQ ID NO: 69)

X$_1$SDIFX$_2$GEPX$_3$LX$_4$PX$_5$X$_6$X$_7$X$_8$; (SEQ ID NO: 70)

SDIFX$_2$GEPX$_3$LX$_4$PX$_5$X$_6$X$_7$X$_8$X$_9$; (SEQ ID NO: 71)

DIFX$_2$GEPX$_3$DC$_4$PX$_5$X$_6$X$_7$X$_8$X$_9$Q; (SEQ ID NO: 72)

IFX$_2$GEPX$_3$LX$_4$PX$_5$X$_6$X$_7$X$_8$X$_9$QL; (SEQ ID NO: 73)

X$_1$SDIFX$_2$GEPX$_3$LX$_4$PX$_5$X$_6$X$_7$X$_8$X$_9$; (SEQ ID NO: 74)

SDIFX$_2$GEPX$_3$LX$_4$PX$_5$X$_6$X$_7$X$_8$X$_9$Q; (SEQ ID NO: 75)

DIFX$_2$GEPX$_3$LX$_4$PX$_5$X$_6$X$_7$X$_8$X$_9$QL; (SEQ ID NO: 76)

X$_1$SDIFX$_2$GEPX$_3$LX$_4$PX$_5$X$_6$X$_7$X$_8$X$_9$Q; (SEQ ID NO: 77)

SDIFX$_2$GEPX$_3$LX$_4$PX$_5$X$_6$X$_7$X$_8$X$_9$QL; (SEQ ID NO: 78)
or

X$_1$SDIFX$_2$GEPX$_3$LX$_4$PX$_5$X$_6$X$_7$X$_8$X$_9$QL; (SEQ ID NO: 79)

wherein X$_1$, X$_2$, X$_3$, X$_4$, X$_5$, X$_6$, X$_7$, X$_8$, X$_9$ are as defined above.

Preferably, in the above defined polypeptide:

X$_1$ represents G, D, or A

X$_2$ represents T or K;

X$_3$ represents S or A;

X$_4$ represents L;

X$_5$ represents D or N;

X$_6$ represents G or S;

X$_7$ represents P;

X$_8$ represents V or M;

X$_9$ represents G, D, E, or A.

In a preferred embodiment of the invention, the above-defined polypeptide comprises, or consists of:

GSDIFTGEPSL; (SEQ ID NO: 80)

SDIFTGEPSLL; (SEQ ID NO: 81)

DIFTGEPSLLP; (SEQ ID NO: 82)

IFTGEPSLLPD; (SEQ ID NO: 83)

FTGEPSLLPDS; (SEQ ID NO: 84)

TGEPSLLPDSP; (SEQ ID NO: 85)

KGEPSLLPDSP; (SEQ ID NO: 86)

GEPSLLPDSPV; (SEQ ID NO: 87)

EPSLLPDSPVG; (SEQ ID NO: 88)

PSLLPDSPVGQ; (SEQ ID NO: 89)

SLLPDSPVGQL; (SEQ ID NO: 90)

GSDIFTGEPSLL; (SEQ ID NO: 91)

SDIFTGEPSLLP; (SEQ ID NO: 92)

DIFTGEPSLLPD; (SEQ ID NO: 93)

IFTGEPSLLPDS; (SEQ ID NO: 94)

FTGEPSLLPDSP; (SEQ ID NO: 95)

TGEPSLLPDSPV; (SEQ ID NO: 96)

GEPSLLPDSPVG; (SEQ ID NO: 97)

EPSLLPDSPVGQ; (SEQ ID NO: 98)

PSLLPDSPVGQL; (SEQ ID NO: 99)

GSDIFTGEPSLLP; (SEQ ID NO: 100)

SDIFTGEPSLLPD; (SEQ ID NO: 101)

DIFTGEPSLLPDS; (SEQ ID NO: 102)

IFTGEPSLLPDSP; (SEQ ID NO: 103)

FTGEPSLLPDSPV; (SEQ ID NO: 104)

TGEPSLLPDSPVG; (SEQ ID NO: 105)

GEPSLLPDSPVGQ; (SEQ ID NO: 106)

EPSLLPDSPVGQL; (SEQ ID NO: 107)

GSDIFTGEPSLLPD; (SEQ ID NO: 108)

SDIFTGEPSLLPDS; (SEQ ID NO: 109)

DIFTGEPSLLPDSP; (SEQ ID NO: 110)

IFTGEPSLLPDSPV; (SEQ ID NO: 111)

FTGEPSLLPDSPVG; (SEQ ID NO: 112)

TGEPSLLPDSPVGQ; (SEQ ID NO: 113)

GEPSLLPDSPVGQL; (SEQ ID NO: 114)

GSDIFTGEPSLLPDS; (SEQ ID NO: 115)

SDIFTGEPSLLPDSP; (SEQ ID NO: 116)

DIFTGEPSLLPDSPV; (SEQ ID NO: 117)

IFTGEPSLLPDSPVG; (SEQ ID NO: 118)

FTGEPSLLPDSPVGQ; (SEQ ID NO: 119)

TGEPSLLPDSPVGQL; (SEQ ID NO: 120)

GSDIFTGEPSLLPDSP; (SEQ ID NO: 121)

SDIFTGEPSLLPDSPV; (SEQ ID NO: 122)

DIFTGEPSLLPDSPVG; (SEQ ID NO: 123)

IFTGEPSLLPDSPVGQ; (SEQ ID NO: 124)

FTGEPSLLPDSPVGQL; (SEQ ID NO: 125)

GSDIFTGEPSLLPDSPV; (SEQ ID NO: 126)

SDIFTGEPSLLPDSPVG; (SEQ ID NO: 127)

DIFTGEPSLLPDSPVGQ; (SEQ ID NO: 128)

IFTGEPSLLPDSPVGQL; (SEQ ID NO: 129)

GSDIFTGEPSLLPDSPVG; (SEQ ID NO: 130)

SDIFTGEPSLLPDSPVGQ; (SEQ ID NO: 131)

DIFTGEPSLLPDSPVGQL; (SEQ ID NO: 132)

GSDIFTGEPSLLPDSPVGQ; (SEQ ID NO: 133)

SDIFTGEPSLLPDSPVGQL; (SEQ ID NO: 134)

GSDIFTGEPSLLPDSPVGQL; (SEQ ID NO: 2)

ASDIFTGEPSLLPDSPVAQL; (SEQ ID NO: 135)

ASDIFTGEPSLLPDSPVGQL; (SEQ ID NO: 136)

GSDIFTGEPSLLPDSPVAQL; (SEQ ID NO: 137)

DSDIFTGEPALLPDSPVEQL; (SEQ ID NO: 138)

YEKLLGSDICTGEPSLLPDSP; (SEQ ID NO: 139)
or

YEKLCGSDIFTGEPSLLPDSPVGQL. (SEQ ID NO: 140)

According to another preferred embodiment, the present invention relates to a polypeptide comprising, or consisting of, an amino acid sequence selected in the group comprising GSD IFT GEP SLL PDS PVG QL (SEQ ID NO: 2) from *Homo sapiens*, from *Macaca mulatta*, from *Pan troglodytes*, from *Felis catus*, GSD IFT GEP SLL PDG PVG QL (SEQ ID NO: 14) from *Canis lupus* familiaris, from *Carollia perspicillata*, DSD IFT GEP SLL PDS PVD QL (SEQ ID NO: 15) from *Rattus norvegicus*, DSD IFT GEP SLL PDD PVG QL (SEQ ID NO: 16) from *Peromyscus maniculatus*, DSD IFT GEP SLL PDG PVG QL (SEQ ID NO: 17) from *Onychomys leucogaster*, GSD IFT GEP SLL PDG PVD QL (SEQ ID NO: 18) from *Cervus elaphus*, GSD IFT GEP SLL PNG PVD QL (SEQ ID NO: 19) from *Equus caballus*, GSD IFT GEP SLL PNG PVD QL (SEQ ID NO: 20) from *Bos taurus*, GSD IFT GEP SLH PDG SVG QL (SEQ ID NO: 21) from *Sus scrofa*, GSD IFT GEP PLF PDG PVS QL (SEQ ID NO: 22) from *Cavia porcellus*, DSD IFK GEP ALL PDS PME QL (SEQ ID NO: 23) from *Mus musculus*, fragments and derivatives thereof.

Preferably also, the polypeptide of the invention comprises (i) an amino acid sequence selected in the group consisting of GSD IFT GEP SLL PDS PVG QL (SEQ ID NO: 2), fragments and derivatives thereof.

According to yet another particular embodiment of the invention, the polypeptide of the invention, in particular under a cyclised form, comprises SEQ ID NO: 13, in particular SEQ ID NO: 2, and preferably comprises less than 28 contiguous amino acids from IL-23p19, in particular human IL-23p19. By way of example, a polypeptide according to this embodiment of the invention is represented by KLLGSDIFTGEPSLLPDSPVGQLHAS (SEQ ID NO: 141).

According to preferred embodiments of the invention, the polypeptide of the invention is a cyclised polypeptide, i.e. is in a cyclised form, for example obtained by the addition of two terminal cysteines to the peptide design before its synthesis, and by a cyclisation step on a reducing medium just after its synthesis. Such cyclisation methods are well-known to one of skill in the art. Thus, the polypeptide according to the invention may comprise one cysteine (C) on the N-terminal end of the above defined sequences, e.g. SEQ ID NO: 2 to 141, and/or one cysteine (C) on the C-terminal end of the above defined sequences, e.g. SEQ ID NO: 2 to 141. As will be clear to one of skill in the art, internal cysteines (C), i.e. cysteines which are within the sequence of the polypeptide, may also be used for cyclisation. Cysteines for cyclisation may either be naturally occurring or be inserted, or substituted, in the sequence of the polypeptide to be cyclised. In addition, the polypeptide may also comprise a tyrosine (Y) at the N-terminal end and/or at the C-terminal end, in particular for attaching the polypeptide to a carrier protein.

The polypeptide of the invention may include post-translational modifications such as glycosylation, acetylation, phosphorylation, modifications with fatty acids and the like, and also modifications of the N- or C-termini such as acetylation, biotinylation, amidation.

The polypeptide of the invention may also include one or more amino acid analogues or derivatives—i.e. including unnatural or non-standard amino acids, such as methylated natural amino acids-, polypeptides with substituted linkages, polypeptides with disulfide bonds between cysteine residues, as well as other modifications known in the art. By way of example, as intended herein, the expression "lysine (K)" preferably encompasses both natural lysine, but also derivatives of lysine, such as methyl-lysine, liable to be used in protein synthesis.

The polypeptide of the invention can be prepared by any method known in the art such as classical solid phase synthesis as described by *Merryfield* (Barany and Merrifield, 1980), or by means of recombinant DNA techniques as described by Maniatis et al. (1982).

According to another preferred embodiment, the polypeptide of the invention is coupled, preferably covalently coupled, with a carrier protein such as the keyhole limpet hemocyanin (KLH), a metalloprotein extracted from the *Megathura crenulata*. Thus, the compound according to the invention may comprise, or consist of, a carrier protein linked to the polypeptide according to the invention.

Other carrier proteins may be used, such as virus-like particles for which specific coupling strategies have been disclosed for cytokines peptides in International patent applications WO 05/117983 (VLP-TNF), WO 00/23955 (VLP-GnRH), and for other self-antigens in WO 02/056905 (VLP-antigens). Other well-known examples of carrier proteins are the Hepatitis B surface Antigen (HBsAg) such as in International patent application WO 04/096849 (HBsAg-Th2, only WIPO version), the Bovine Serum Albumin (BSA) or its modified cationized form (cBSA), the diphtheria toxoid (DT), the tetanus toxoid (TT).

A covalent coupling of the polypeptide of the invention can be obtained with a coupling agent such as bis-diazotized benzidine (BDB). Many other coupling agents can be also used beside BDB (Glazer et al., 1975) for instance glutaraldehyde (Habeeb and Hiramoto, 1968), carbodiimides (Goodfriend et al., 1964; Glazer et al., 1975), and m-maleimidobenzoyl-n-hydroxysuccinimide ester or MBS (Kitagawa and Aikawa, 1976).

According to a further preferred embodiment, the polypeptide of the invention or the compound of the invention comprises at least one another amino acid sequence corresponding to an epitope, which epitope is derived from a protein distinct from IL-23.

Another aspect of the invention relates to a nucleic acid encoding for a polypeptide as described above and to a vector comprising said nucleic acid.

Said nucleic acid corresponds to RNA or DNA, preferably to DNA.

Advantageously, said nucleic acid is operatively linked to a promoter sequence, such as a mammalian or a viral promoter, which promoter sequence directs its expression of nucleic acid within a prokarotic or an eukaryotic cell, preferably within an eukaryotic cell.

The nucleic acid encoding for the polypeptide of the invention may be delivered in vivo alone or in association with a vector.

The vectors useful in the invention include, but are not limited to, plasmids, and viruses.

Another aspect of the invention relates to an antibody directed against the polypeptide of the invention, which antibody recognizes the region of human IL-23p19 from $Gly^{105}$ to $Leu^{124}$ (SEQ ID NO: 24) or the region of mouse IL-23p19 from $Asp^{106}$ to $Leu^{125}$ (SEQ ID NO: 3). The present invention also relates an antibody, a scFV or an aptamer which is specific for a polypeptide as defined above, and to pharmaceutical compositions comprising them. Preferably, the antibodies, scFvs, and aptamers of the invention are said to be specific when they present substantially no binding to polypeptides different from those of the invention, such as the polypeptides described in International application WO 03/084979, in conditions where they can bind to polypeptides according to the invention. Preferably also, the antibodies, scFvs and aptamers of the invention are neutralizing, i.e. are liable to prevent the in vivo action of IL-23, for instance by preventing the binding of IL-23 to its target receptor.

Said antibody according to the invention may be a monoclonal or a polyclonal antibody, preferably said antibody is a monoclonal antibody. As will be clear to one of skill in the art an "antibody" according to the invention encompasses whole antibodies as well as antigen-binding antibody fragments, such as Fab and F(ab')2 fragments.

Single-chain Fv fragments (scFvs) are well-known to one of skill in art and may be easily obtained by one of skill in the art. By way of example, anti-IL-23 scFvs are described in Mabry et al. (2010) *Protein Eng. Des. Sel.* 23:115-27. Aptamers are nucleic acids, in particular RNAs, liable to specifically bind to a molecular target, such as a protein. Aptamers may be easily obtained by one of skill in the art, in particular by implementing the well-known SELEX method. Anti-IL-23 aptamers are notably described in Burmeister et al. (2006) *Oligonucleotides* 16:337-51.

The antibody of the invention can be prepared according to well known methods by immunization with a compound or a polypeptide according to the invention, or with a peptide derived from human IL-23p19 region from $Gly^{105}$ to $Leu^{124}$ or from the mouse IL-23p19 region from $Asp^{106}$ to $Leu^{125}$ as described above.

Another aspect of the invention relates to a pharmaceutical composition comprising a pharmaceutically acceptable vehicle in association with, in particular as an active substance, at least one compound as defined above, a polypeptide as described above, a nucleic acid encoding thereof, or a nucleic acid vector comprising said nucleic acid.

Advantageously, the pharmaceutical composition of the invention further comprises at least one adjuvant, so as preferably to induce an optimal antibody response. Adjuvants can be any water-in-oil emulsions for instance complete or incomplete Freund's adjuvants, ISA51, any mineral matrix such as Alum or calcium phosphate or any other type of adjuvant suitable for mammals, in particular humans, and able to induce the production of antibodies.

Advantageously, the pharmaceutical composition of the invention is an immunizing composition, more advantageously a vaccine.

By adjuvant, the present invention refers to any suitable chemical compound supporting the production of a sufficient immune response, such as water in oil suspensions, alum, montanide ISA 51.

Another aspect of the invention relates to the use of at least one compound as defined above, a polypeptide as described above, a nucleic acid sequence coding therefore, a vector comprising such a nucleic acid sequence, or a pharmaceutical composition as described previously for preventing or treating an immune-related disease or a bone resorption disease in a subject, or for the manufacture of a medicament intended for treating an immune-related disease or a bone resorption disease in a subject. The present invention also relates to a compound as defined above, a pharmaceutical composition as defined above, a polypeptide as described above, a nucleic acid sequence coding therefore, a vector comprising such a nucleic acid sequence, for use in the prevention or treatment of an immune-related disease or a bone-resorption disease in a subject.

As used herein, the term "subject" denotes a Mammal, and preferably a human. Accordingly, the subject according to the invention may be an animal or a human.

As intended herein, the expression "bone resorption diseases" relates to any disease involving an excessive, pathological resorption of bone tissues, such as osteoporosis for instance.

As used herein, the term "immune-related disease" relates to a disease in which the immune system is involved in the pathogenesis of the disease, or in which cell proliferation occurs. Examples of immune-related diseases object of this invention are inflammatory diseases, in particular autoimmune diseases, and cancers.

As used herein, the term "immune-related disease" relates more specifically to a disease where IL-23 production is directly or indirectly linked with deleterious effects for the organism.

As used herein, the term "inflammatory disease" relates to any abnormal condition characterized by inflammation, with an excessive accumulation of inflammatory cells in one or several organs such as the skin, brain, digestive tract, kidney, blood, liver, eye, and bone-marrow.

For instance, the term "inflammatory diseases" in this invention can relate to bone-related diseases such as rheumatoid arthritis and ankylosing spondylitis, to skin-related diseases such as psoriasis and psoriatic arthritis, to disorders of the gastrointestinal tract (inflammatory bowel diseases, IBD) such as Crohn's disease and ulcerative colitis, to inflammatory diseases of the brain such as multiple sclerosis, to autoimmune diseases such as autoimmune diabetes, autoimmune thyroid disease, autoimmune hepatitis, and finally to any other non-organ-specific immune-mediated disorder such as systemic lupus erythematosus.

As used herein, the term "cancer" relates to any condition marked by the abnormal proliferation of cells. The proliferative disorder aimed in this invention relates more specifically to certain forms of tumours, where IL-23 plays a pathogenic role.

Advantageously, said cancer is a colo-rectal cancer.

Another aspect of the invention relates to a method for preventing or treating an immune-related disease or a bone resorption disease in a subject, comprising administrating to the subject a therapeutically effective amount of at least one compound as defined above, a polypeptide as described above, a nucleic acid sequence coding therefore, a vector comprising such a nucleic acid sequence, or a pharmaceutical composition as described previously.

Said bone resorption and immune-related diseases are as described previously.

In particular, said cancer is as described previously and, preferably, said cancer is a colo-rectal cancer.

According to the present invention, an "effective amount" of a compound is one which is sufficient to achieve a desired biological effect, in this case for instance inducing the production of antibodies recognizing the region of human IL-23p19 from $Gly^{105}$ to $Leu^{124}$ or the region of mouse IL-23p19 from $Asp^{106}$ to $Leu^{125}$. It is understood that the effective dosage will be dependent upon the age, sex, health, and weight of the recipient, kind of concurrent treatment, if any, frequency of treatment, and the nature of the effect desired. Preferably, the immunizing dose of peptide may vary from 1 μg of peptide in the immunizing composition to 2 mg of peptide in the immunizing composition. Possibly, the doses will vary between 20 μg to 400 μg per dose of immunizing composition. Typically, it will vary between 50 μg to 200 μg per immunizing composition.

In the following, the invention is described in more detail with reference to amino acid sequences, nucleic acid sequences and the examples. Yet, no limitation of the invention is intended by the details of the examples. Rather, the invention pertains to any embodiment which comprises details which are not explicitly mentioned in the examples herein, but which the skilled person finds without undue effort.

EXAMPLES

Example 1

Immunisation Against a Peptide from hIL-23 and Cross-Reactivity, Against Murine IL-23, of the Purified Sera Specific-pathogen-free New Zealand rabbits (n=4) are immunized with 100 μg of a peptide derivative of human IL-23 by five immunizations in CFA/IFA at day 0, 14, 28, 56 and 70. The peptide, whose sequence is C-GSD IFT GEP SLL PDS PVG QL-C-Y, was coupled to KLH with BDB. The sera from immunized rabbits were taken at day 82 after initial immunization, and the antibodies were purified by affinity chromatography against protein A. The purified antibodies were tested by ELISA at various dilutions and on a plate coated either by human IL-23 or by murine IL-23 (cf. FIG. 1). The mean OD value of the 6 purified sera is given at the various dilutions for the ELISA tests against murine IL-23 (dotted line) and against human IL-23 (regular line).

Example 2

Neutralization of the Biological Activity of Human IL-23 after Immunization Against a Peptide Derived from Human IL-23

Figure 2:
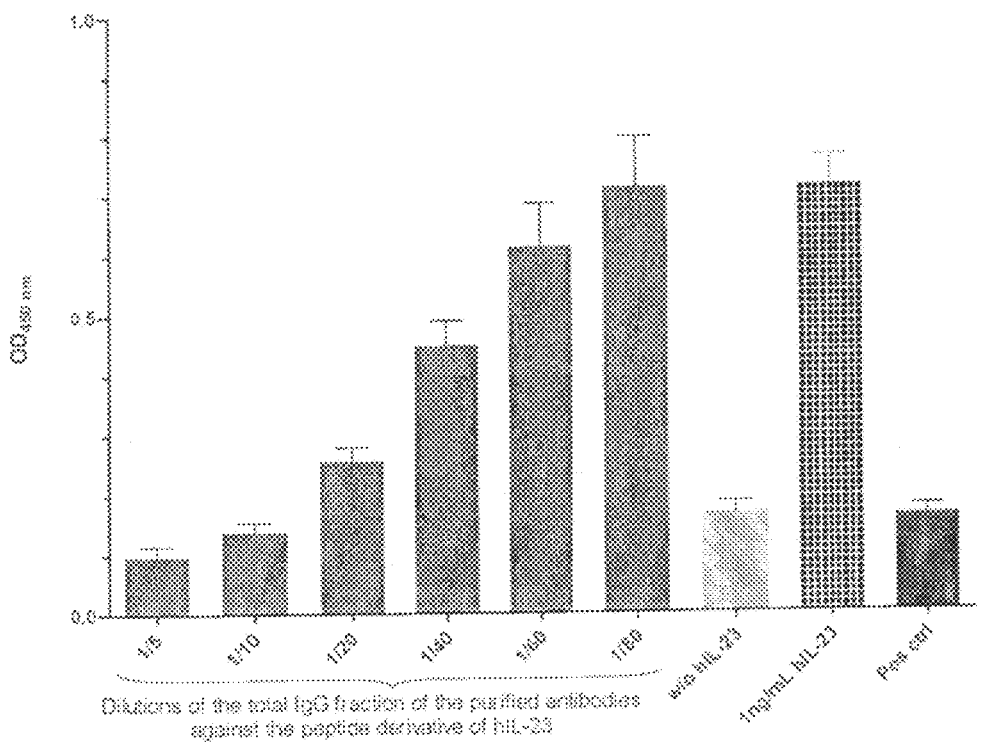
FIG. 2 shows the neutralization of the biological activity of human IL-23 by antibodies purified from rabbits immunized against a human IL-23 peptide.

The neutralization capacity of the purified total IgG fraction derived from the 4 immunized rabbits of example 1 was then tested in a neutralization assay for human IL-23. The test is based on the fact that purified mouse splenocytes secrete IL-17 in a dose dependent fashion, in response to the stimulation with bioactive human IL-23 (cf. FIG. 2). On the x-axis one can see the various dilutions of the IgG tested and on the y-axis the production of IL-17 as an optical density value. One sees that the IgG fraction of rabbits immunized against the peptide neutralize the biological activity of human IL-23 in a dose-dependent fashion. Each bar represents the mean of the tests performed with the 4 purified antibodies; the standard deviation is also indicated. The experimental conditions comprise two negative controls (no human IL-23 and no inhibitor) and a positive control with an anti-hIL-23 neutralizing antibody sold from the company R&D Systems (# ref: AF1716).

Example 3

Neutralization of the Biological Activity of Murine IL-23 after Immunization Against a Peptide Derived from Human IL-23

Figure 3:
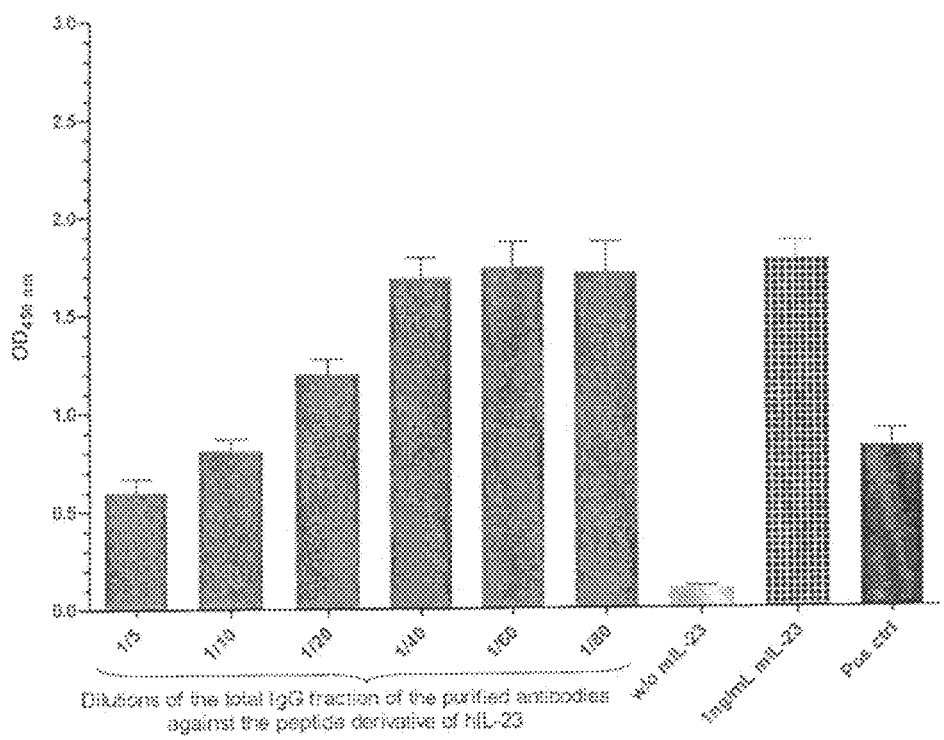
FIG. 3 shows the neutralization of the biological activity murine IL-23 by antibodies purified from rabbits immunized against a human IL-23 peptide.

The same IgG fraction from 4 immunized rabbits used in example 2 is used for a test of neutralization of the murine IL-23 cytokine. The test for murine IL-23 is based on the fact that purified mouse splenocytes secrete IL-17 in a dose dependent fashion, in response to the stimulation with bioactive human IL-23 (cf. FIG. 3). One sees that the IgG fraction of rabbits immunized against the human IL-23 peptide can neutralize the biological activity of murine IL-23 in a dose-dependent fashion. Each bar represents the mean of the tests performed with the 4 purified antibodies; the standard deviation is also indicated. There are two negative controls (no mouse IL-23 and no inhibitor) and a positive control with an anti-murine IL-23 neutralizing antibody sold from the company R&D Systems (# ref: AF1619).

Example 4

Neutralization of the Biological Activity of Murine IL-23 and Human IL23 after Immunization Against a Peptide Derived from Murine IL-23

Figure 4A:
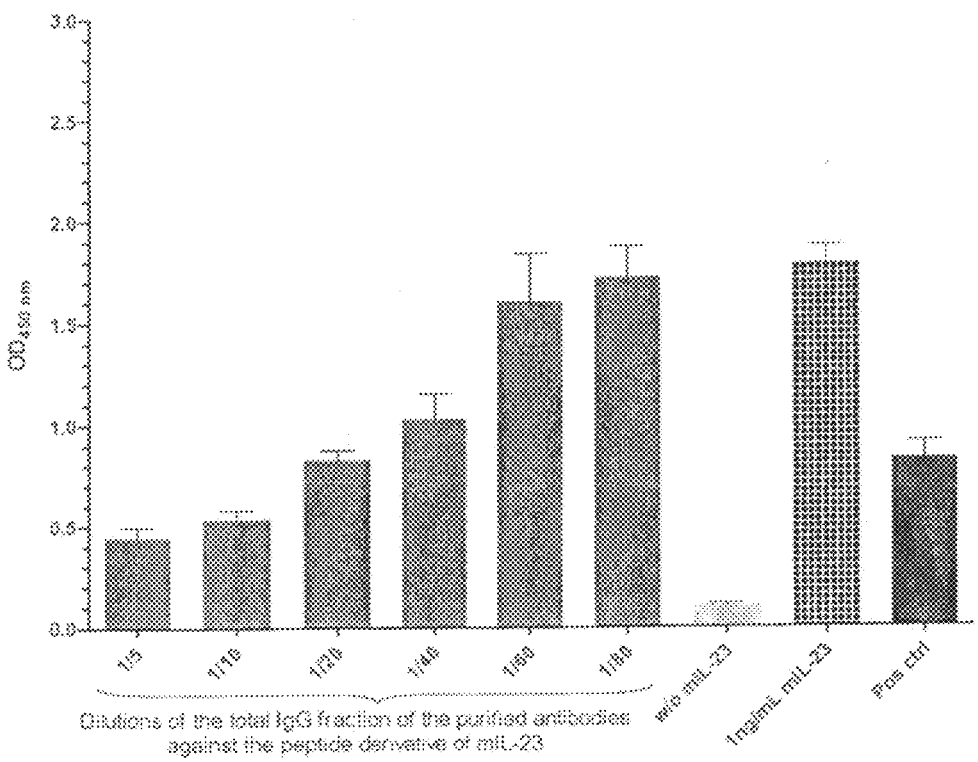
FIG. 4A shows the neutralization of the biological activity murine IL-23 by antibodies purified from rabbits immunized against a murine IL-23 peptide.
Figure 4B:
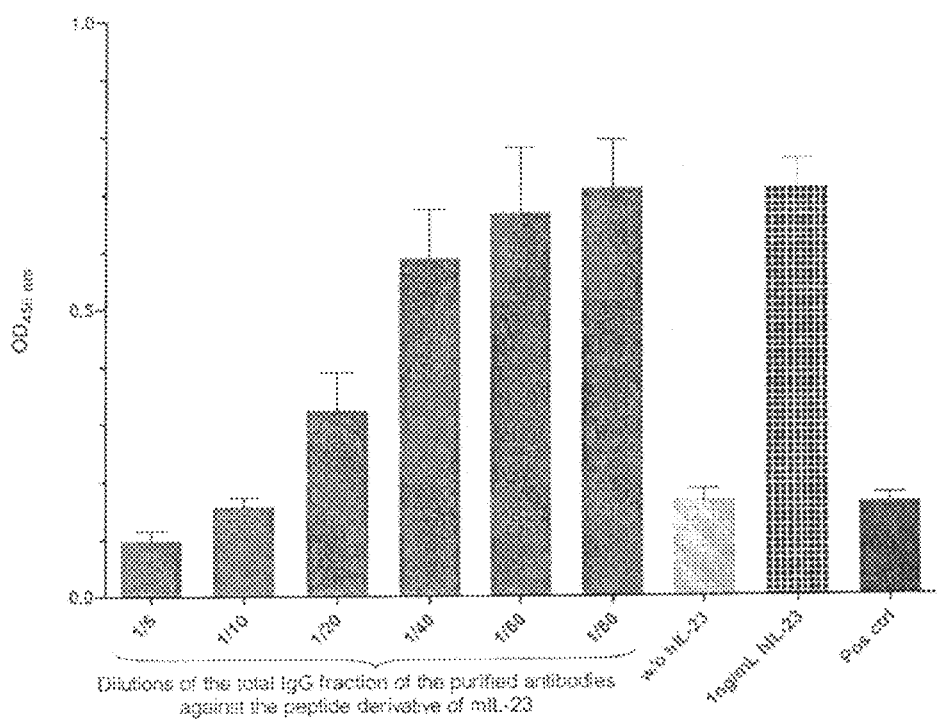
FIG. 4B shows the neutralization of the biological activity human IL-23 by antibodies purified from rabbits immunized against a murine IL-23 peptide.

Specific-pathogen-free New Zealand rabbits (n=4) are immunized with 100 µg of a peptide derivative of murine IL-23 by five immunizations in CFA/IFA at day 0, 14, 28, 56 and 70. The peptide, whose sequence is C-DSD IFK GEP ALL PDS PME QL-C was coupled to KLH with glutaraldehyde. The sera from immunized rabbits were taken at day 82 after initial immunization, and the antibodies were purified by affinity chromatography against protein A. Neutralization assays against mIL-23 (FIG. 4A) and against hIL-23 (FIG. 4B) were performed as described in example 2 and example 3. One sees that the purified rabbit antibodies (obtained after immunization against a peptide of mIL-23) can neutralize mIL-23 (FIG. 4A) and also cross-neutralize hIL-23 (FIG. 4B).

Example 5

Kinetics of the Auto-Antibodies Against Murine IL-23 in Mice Immunized with Peptide Derivatives of IL-23

Figure 5:
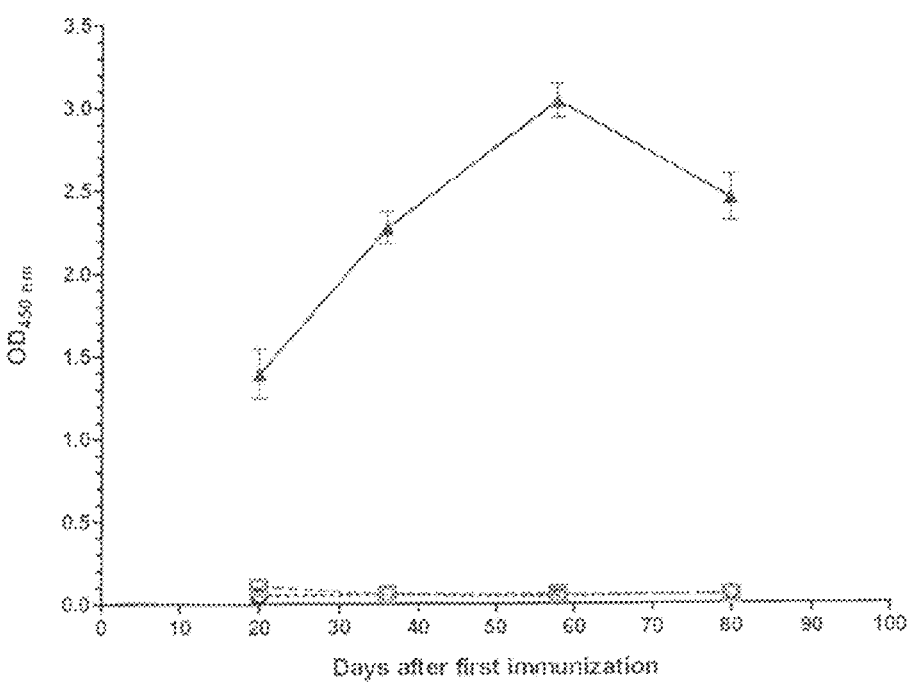
FIG. 5 shows the kinetics of the antibody response in mice immunized against a murine IL-23 peptide.

A peptide of murine IL-23 is coupled to KLH in the presence of a coupling agent (BDB). The peptide has been cyclised thanks to the addition of 2 cysteine residues coupled to BDB through an additional tyrosine; its amino-acid sequence is: C-DSD IFK GEP ALL PDS PME QL-C-Y. The vaccinal composition is injected intra-muscularly three times in ten (10) OF1 mice, at a dose of 100 µg/injection once every 2 weeks at days 0, 15, 30, 45. The sera of the animals are taken after the boosts at days 20, 38, 60 and 80 and are tested by ELISA at a dilution of 1/500 and on a coating of murine IL-23. The ELISA results are given as optical density ($OD_{450nm}$) values. FIG. 5 presents the mean $OD_{450nm}$ value obtained at each time-point for the 10 mice tested. The grey line represents the response of mice immunized with the peptide derivative of IL-23 (triangles). The dotted lines represents the response of control mice immunized with the vehicle (empty grey diamonds), and control mice immunized with the carrier protein only (empty grey squares).

Example 6

Crossreactivity of Rabbit Anti-Murine IL-23 Peptide Antibodies with Murine and Human IL-23

Four New Zealand rabbits were immunized with the cyclised peptide Y-C-KGE PAL LPD SP-C derived from the murine IL-23, similarly as in the protocol described in Example 1. The peptide was coupled with KLH via BDB and a supplementary tyrosine. The sera of the animals were purified by affinity column against protein A and the purified antibodies were tested in ELISA and in neutralisation assays. For ELISA, plates were coated either with murine or with human IL-23 and individual sera were tested at different dilutions to determine the $Titer_{50}$. The mean antibody titer against mouse and human IL-23 are given in Table 1. The titer corresponds to the dilution corresponding yielding an OD value at 50% of the maximal OD score (obtained for the smallest dilution, 1/50e). In parallel, different dilutions of the purified rabbit antibodies were tested on IL-23 neutralisation assays, similarly as in Examples 2, 3, and 4. Table 1 presents the average neutralisation obtained for the 4 purified antibodies rabbit at a dilution of 1/20 and in the presence of 1 ng/mL of bioactive mIL-23 or hIL-23. Results demonstrate a neutralization capacity of the rabbit anti-murine IL-23 peptides antibodies against both murine and human bioactive IL-23.

TABLE 1

| Immunogen: modified murine IL-23 peptide Y—C-KGE PAL LPD SP-C | | |
|---|---|---|
| | Human IL-23 | Murine IL-23 |
| Average $Titer_{50}$ (ELISA), SD | 1454, ± 113 | 5402, ± 245 |
| Average % neutralization, SD | 57%, ± 8% | 72%, ± 7% |

Example 7

Crossreactivity of the Rabbit Anti-Human IL-23 Peptides Antibodies with Murine and Human IL-23

Similarly as in Example 6, four rabbits were immunized with the cyclised peptide Y-C-TGE PSL LPD SP-C derived from human IL-23. The peptide was coupled with KLH via BDB and a supplementary tyrosine. The resulting sera were purified before testing on ELISA and neutralization assays under the same conditions. The tested sera (cf. Table 2) also demonstrated significant antibody titers and a neutralizing capacity against both human and murine IL-23, in a similar fashion as in the previous example.

TABLE 2

| Immunogen: modified human IL-23 peptide Y—C-TGE PSL LPD SP-C | | |
|---|---|---|
| | Human IL-23 | Murine IL-23 |
| Average $Titer_{50}$ (ELISA), SD | 8415, ± 322 | 2740, ± 141 |
| Average % neutralization, SD | 78%, ± 9% | 34%, ± 7% |

Example 8

Peptides Derived from Human IL-23 of Size 5 are Able to Induce Antibodies Recognizing Human IL23

Similarly as in Example 6, three rabbits were immunized with the peptide 1 derived from hIL-23, C-TGE PS-C coupled with KLH via glutaraldehyde, and three rabbits were immunized with peptide 2 derived from hIL-23, C-LPD SP-C-Y coupled with KLH via BDB. The resulting sera were purified on a protein A column before testing on ELISA and neutralization assays against hIL-23. As shown in Table 3, the tested sera demonstrated significant antibody titers and a neutralizing capacity against human IL-23.

TABLE 3

Responses of the purified serum antibodies against peptides of hIL-23

|  | Peptide CTGEPSC | Peptide CLPDSPC-Y |
|---|---|---|
| Average Titer$_{50}$ (ELISA), SD | 1758 ± 153 | 2287 ± 175 |
| Average % neutralization, SD | 35 ± 7% | 39 ± 11% |

Example 9

Clinical and Histological Protection Following Vaccination Against a Peptide Derivative of Murine IL-23 in a Mouse Model of Rheumatoid Arthritis The collagen-induced arthritis is a well-known model of rheumatoid arthritis, which reproduces the main features characterizing the human disease. The experimental disease is induced in the animal by two successive injections of type II bovine collagen in the tail. Clinical signs of disease occur a few days later, principally marked by a severe articular inflammation and the joint destruction. The articular inflammation can be quantified and reported as clinical scores by the man of the art: a score from 0 (no clinical sign) to 4 (total inflammation) is given for each articulation of each mouse. Groups of 10 mice are compared by the mean value of the scores obtained on one mouse. Similarly, the articular inflammation and destruction can be observed on histological sections of joints and be reported as histological scores by the man of the art.

Figure 6A:
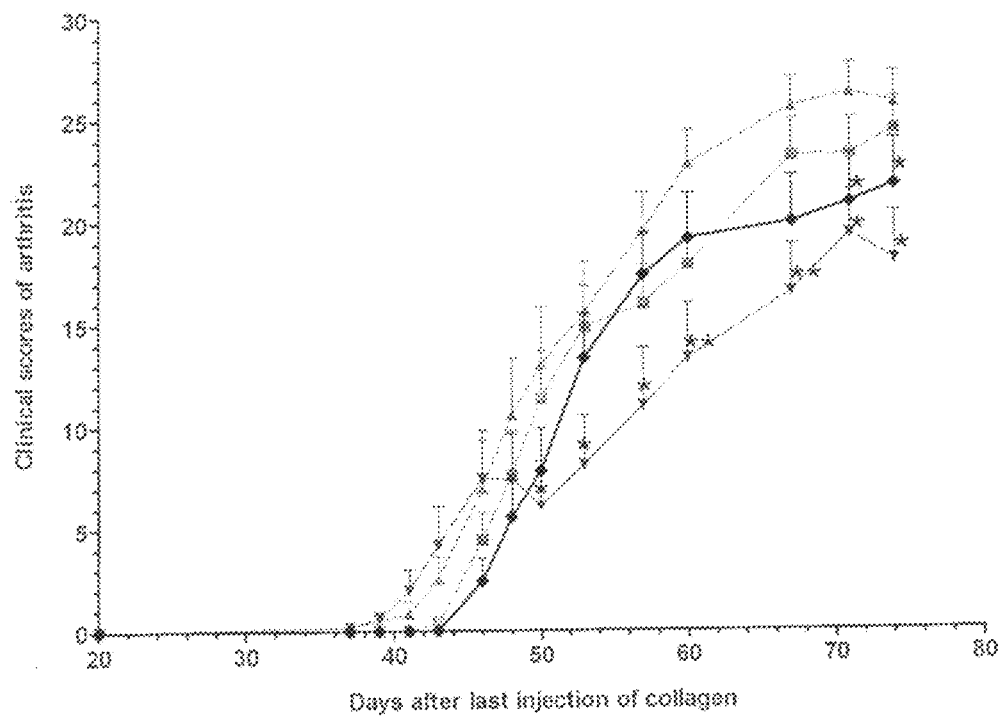
FIG. 6 shows the clinical (FIG. 6A) and histological (FIG. 6B, FIG. 6C) protection incurred by the vaccination against a peptide derivative of murine IL-23 in a mouse model of rheumatoid arthritis (collagen-induced arthritis).
Figure 6B:
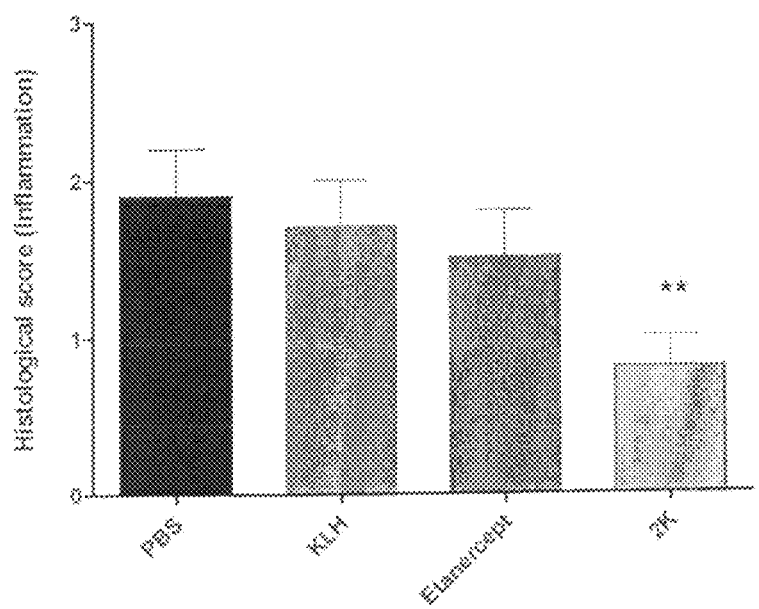
Figure 6C:
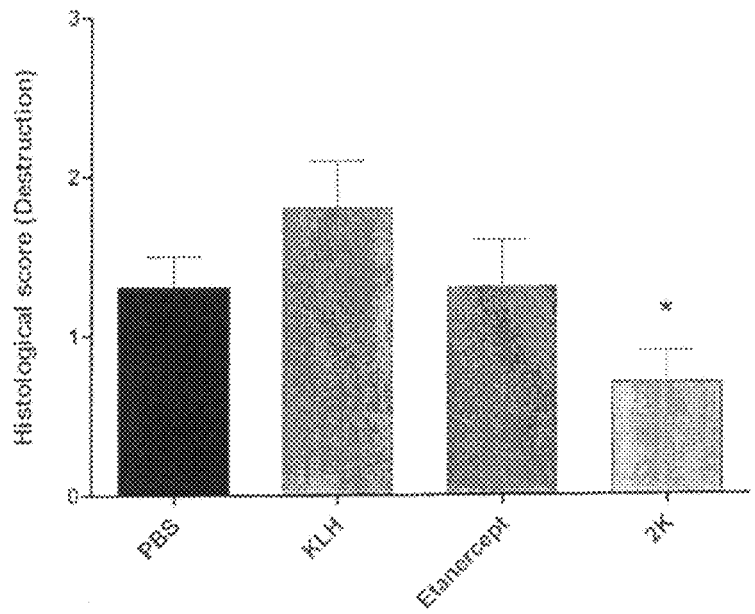

DBA/1 mice (n=10 per treatment group) were vaccinated two weeks before the first injection of collagen either with the cyclised peptide derived from mIL23: C-DSD IFK GEP ALL PDS PME QL-C-Y (coupled with KLH via BDB and an additional tyrosine on the C-terminus), or with a control made of KLH alone, or with PBS alone. The injected dose in each mice corresponded to 100 µg of coupled peptide for the peptide group, and to 100 µg of KLH alone for the KLH control group, all in complete Freund's adjuvant. One boost was made in incomplete Freund's adjuvant (ISA51) between the two injections of collagen and finally one last boost was given eight days after the second injection of collagen also in incomplete Freund's adjuvant. Clinical signs of the disease appeared concomitantly to the last immunization and clinical scores progressively rose for each diseased animal until the day 80 (after the first collagen immunization) at which the animals were euthanized for ethical reasons. Results show that the treatment by anti-IL-23 vaccine (inverted triangles) gives a statistically significant protection at the late stage of disease (cf. FIG. 6A), similar to the one provided by the currently used drug Etanercept (stars). Interestingly, vaccination with the peptide derivative of murine IL-23 also limits the extent of both the articular inflammation and destruction at the histological level (cf. FIGS. 6B and 6C, respectively in which the IL-23 peptide immunized-group is labelled as "2K").

Example 10

Clinical Protection Following Vaccination Against a Peptide Derivative of Murine IL-23 in a Mouse Model of Multiple Sclerosis The experimental autoimmune encephalomyelitis in mice is a well-known model of multiple sclerosis. Three groups of 12 C57BL/6 mice were injected 4-times (s.c.) either with 1/100 µg/animal of the same peptide derivative of murine IL-23 as in example 9 coupled with KLH and emulsioned in CFA for the initial immunization and IFA (ISA51) for the subsequent boosts, or with 2/the carrier protein prepared in the same conditions, or with 3/PBS alone. The injections took pace at day 0, 15, 30 and 45.

Figure 7:
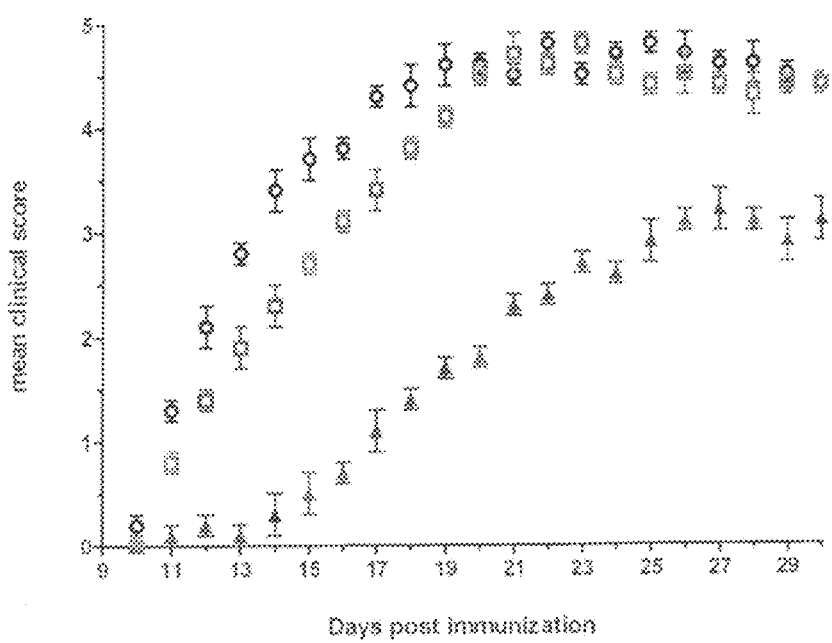
FIG. 7 shows the clinical protection following vaccination against a peptide derivative of murine IL-23 in a mouse model of multiple sclerosis.

To induce the experimental disease, mice were immunized (s.c.) at two sites with 200 µg of MOG peptide 35-55 in 400 µg of Complete Freund's Adjuvant (CFA) at day 60. On the same day and after two days, mice were injected (i.p.) with, respectively 75 and 200 ng/mouse, of pertussis toxin (List Biological Laboratories). The mice were then assessed daily for clinical signs of EAE according to the following well-known scoring method (Sinha et al., *J. Immunol.*, 2008): 0, normal; 0.5, limp tail; 1, tail paralysis; 2, mono or paraparesis of the hind limbs; 3, mono or paraplegia of the hind limbs; 4, paraplegia of the forelimb; 5, moribund condition or death. The follow-up was done on a period of 30 days as shown (cf. FIG. 7). The mice immunized against the IL-23 peptide (triangles) exhibited a statistically significant lower disease activity than the two control groups (p=0.0003).

The invention claimed is:

1. A method of vaccination for protecting against articular inflammation in rheumatoid arthritis and multiple sclerosis, comprising administering to a subject in need thereof a compound comprising or consisting of a cyclized polypeptide to a subject in need thereof, wherein the cyclized polypeptide comprises a sequence having at least 90% identity with SEQ ID NO:2 and has a length equal to or less than 28 amino acid residues, or consists of a sequence having at least 90% identity with SEQ ID NO:2, and elicits antibodies directed against human IL-23.

2. The method of claim 1, wherein the compound is administered as a pharmaceutical composition further comprising a pharmaceutically acceptable vehicle.

3. The method of claim 1, wherein the polypeptide comprises or consists of the sequence of SEQ ID NO:2 and has a length equal to or less than 28 amino acid residues.

4. The method of claim 1, wherein the compound comprises a carrier protein linked to the polypeptide.

5. The method of claim 2, wherein the pharmaceutical composition further comprises an adjuvant.

6. A method of vaccination for protecting against articular inflammation in rheumatoid arthritis and multiple sclerosis, comprising administering to a subject in need thereof a compound comprising or consisting of a cyclized polypeptide, wherein the cyclized polypeptide comprises the sequence of SEQ ID NO:2 and has a length equal to or less than 28 amino acid residues.

7. The method of claim 6, wherein the compound is administered as a pharmaceutical composition further comprising a pharmaceutically acceptable vehicle.

8. The method of claim 7, wherein the pharmaceutical composition further comprises an adjuvant.

9. The method of claim 6, wherein the compound comprises a carrier protein linked to the polypeptide.

10. A method for eliciting anti-IL-23 antibodies in a subject, comprising administering a compound comprising or consisting of a cyclized polypeptide to the subject, wherein the cyclized polypeptide comprises a sequence having at least 90% identity with SEQ ID NO:2 and has a length equal to or less than 28 amino acid residues, or consists of a sequence having at least 90% identity with SEQ ID NO:2, and elicits antibodies directed against human IL-23.

11. The method of claim 10, wherein the cyclized polypeptide comprises the sequence of SEQ ID NO:2 and has a length equal to or less than 28 amino acid residues, or consists of the sequence of SEQ ID NO:2.

12. The method of claim 10, wherein the compound is administered as a pharmaceutical composition further comprising a pharmaceutically acceptable vehicle.

13. The method of claim 12, wherein the pharmaceutical composition further comprises an adjuvant.

14. The method of claim 10, wherein the compound comprises a carrier protein linked to the polypeptide.

\* \* \* \* \*